US011309087B2

(12) United States Patent
Holcomb

(10) Patent No.: US 11,309,087 B2
(45) Date of Patent: Apr. 19, 2022

(54) METHOD FOR THE COMPUTATION OF VORONOI DIAGRAMS

(71) Applicant: Jeffrey W. Holcomb, Irving, TX (US)

(72) Inventor: Jeffrey W. Holcomb, Irving, TX (US)

( * ) Notice: Subject to any disclaimer, the term of this patent is extended or adjusted under 35 U.S.C. 154(b) by 559 days.

(21) Appl. No.: 14/554,052

(22) Filed: Nov. 26, 2014

(65) Prior Publication Data

US 2016/0147973 A1 May 26, 2016

(51) Int. Cl.
*G06T 15/00* (2011.01)
*G16H 50/50* (2018.01)

(52) U.S. Cl.
CPC ............ *G16H 50/50* (2018.01); *G06T 15/00* (2013.01)

(58) Field of Classification Search
CPC ......... G06T 15/00; G06T 15/04; G06T 15/10; G06T 15/20; G06F 17/5018
See application file for complete search history.

(56) References Cited

U.S. PATENT DOCUMENTS

| 248,567 | A | | 10/1881 | Applegate |
|---|---|---|---|---|
| 5,537,519 | A | * | 7/1996 | Vossler .................... G06T 17/10 345/420 |
| 5,886,702 | A | | 3/1999 | Migdal |
| 6,088,511 | A | | 7/2000 | Hardwick |
| 6,133,921 | A | | 10/2000 | Turkiyyah |
| 6,182,016 | B1 | | 1/2001 | Liang |
| 6,393,159 | B1 | | 5/2002 | Prasad |
| 7,240,306 | B2 | | 7/2007 | Allen |
| 7,634,395 | B2 | * | 12/2009 | Flandrin ................. G06T 17/20 345/419 |
| 7,679,615 | B2 | | 3/2010 | Kim |
| 7,765,071 | B2 | | 7/2010 | Kim |
| 7,825,927 | B2 | | 11/2010 | Kim |
| 8,004,517 | B1 | * | 8/2011 | Edelsbrunner .......... G06T 17/20 345/419 |
| 8,411,952 | B2 | | 4/2013 | Chefd'hotel |
| 8,442,805 | B2 | | 5/2013 | Reem |
| 8,681,145 | B2 | * | 3/2014 | Tamstorf ................. G06T 13/20 345/419 |
| 8,737,769 | B2 | | 5/2014 | Finch |
| 9,305,396 | B2 | * | 4/2016 | Mason .................... G06T 17/10 |

(Continued)

OTHER PUBLICATIONS

Bharaj, G., Thormahlen, T., Seidel, H., Theobalt, C.: Automatically Rigging Multi-component Characters. Eurographics, vol. 31 (2012) 755-764.

(Continued)

*Primary Examiner* — William V Gilbert

(57) ABSTRACT

Two methods are provided for the automated derivation of Voronoi diagrams in 3D. The invention, implementable via various means such as a processing system, method, or data structure in a recording medium such as memory or as a self-contained electronic circuit, has wide ranging applicability to numerous fields such as big data analysis, computer graphics and animation, route planning, collision avoidance, computer vision, robotic vision, and etc. The first method of the invention details steps necessary to segment data according to a set of generators so as to produce a Voronoi partitioning of the data. The second method of the invention includes steps associated with the derivation of the mathematical specification of a 3D Voronoi diagram.

7 Claims, 16 Drawing Sheets

(56) References Cited

U.S. PATENT DOCUMENTS

| | | | | |
|---|---|---|---|---|
| 2002/0038201 A1* | 3/2002 | Balaven | ............... | G06T 17/20 |
| | | | | 703/2 |
| 2013/0166264 A1* | 6/2013 | Usadi | ............... | G06F 17/5009 |
| | | | | 703/2 |
| 2015/0079327 A1* | 3/2015 | Kautz | ............... | B29C 67/0088 |
| | | | | 428/64.1 |
| 2015/0112653 A1* | 4/2015 | Wu | ............... | G06F 17/5009 |
| | | | | 703/2 |
| 2015/0254209 A1* | 9/2015 | Levy | ............... | G06F 17/10 |
| | | | | 703/2 |
| 2016/0371881 A1* | 12/2016 | Tokuyoshi | ............... | G06T 15/04 |
| 2017/0032568 A1* | 2/2017 | Gharpure | ............... | G06T 17/00 |

OTHER PUBLICATIONS

Chen, X., Golovinskiy, A., Funkhouser, T.: A Benchmark for 3D Mesh Segmentation. ACM Trans. Graph, vol. 28 (2009) 73:1-73:12.

Cheddad, A., Mohamad, D., and Manaf, A.: Exploiting Voronoi Diagram Properties in Face Segmentation and Feature Extraction, Pattern Recognition, 41 (2008) 3842-3859.

Delahaye, D. and Puechmorel, S.: 3D Airspace Sectoring by Evolutionary Computation, Proceedings of the 8th Annual Conference on Genetic and Evolutionary Computation (2006) 163.

Watson, D. F.: Computing the n-dimensional Delaunay Tessellation with Application to Voronoi Polytopes, The Computer Journal, vol. 24, No. 2 (1981) 167-172.

\* cited by examiner

Fig. 6
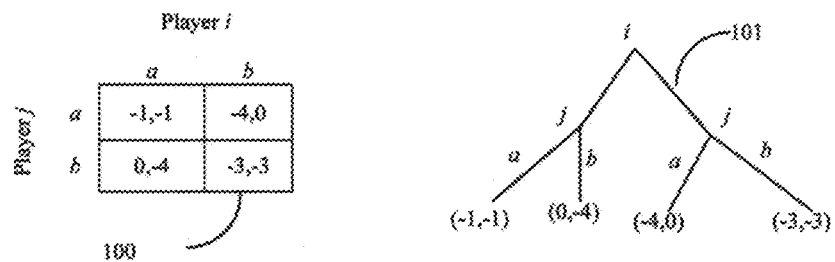
Fig. 7
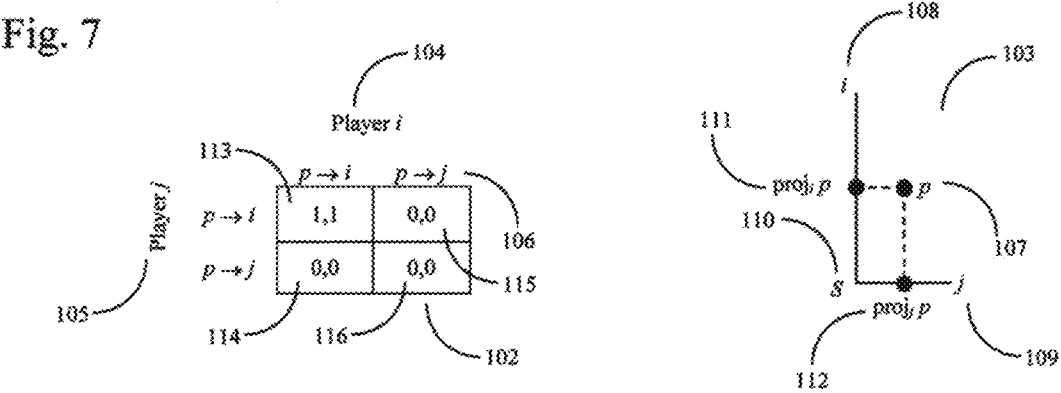
Fig. 8

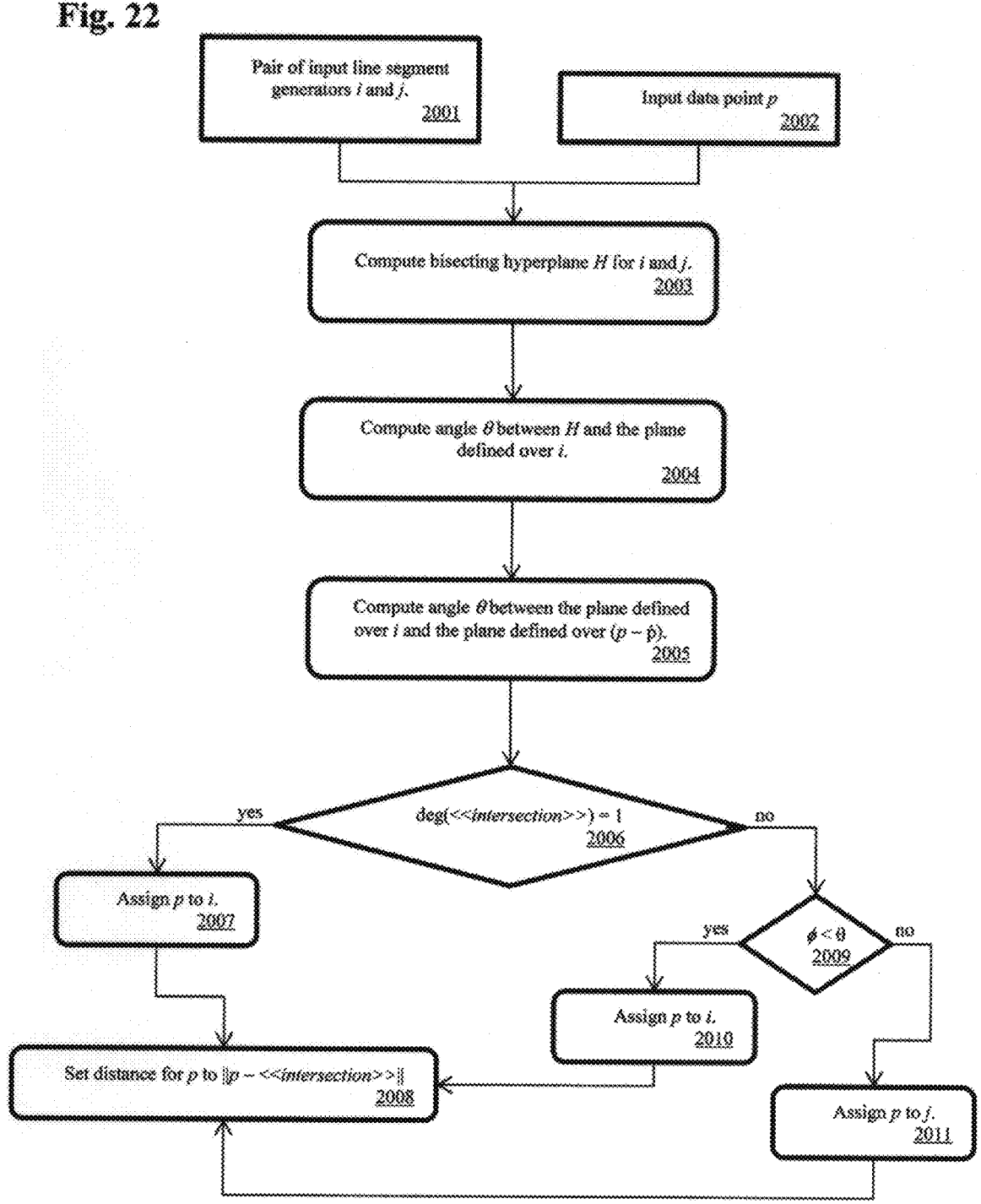

METHOD FOR THE COMPUTATION OF VORONOI DIAGRAMS

REFERENCES CITED

U.S. Patent Documents

U.S. Pat. No. 7,679,615 B2 March 2020 Kim et al.
US20140300597 A1 April 2013 Holcomb

OTHER PUBLICATIONS

I. Boada, N. Coll, N. Madero, and J. A. Sellares, "Approximations of 2D and 3D generalized Voronoi diagrams," International Journal of Computer Mathematics, vol. 85, pp. 1003-1022, July 2008.
M. Held, S. Huber, "Topoloty-oriented incremental computation of Voronoi diagrams of circular arcs and straight-line segments," Computer-Aided Design, vol. 41, pp. 327-338, July 2009.
M. Held, "VRONI: An engineering approach to the reliable and efficient computation of Voronoi diagrams of points and line segments," Computational Geometry, vol. 18, pp. 95-123, July 2001.

TECHNICAL FIELD

This invention relates to the automatic generation, derivation, and/or construction of Voronoi diagrams/graphs, and the automatic partitioning of data according to an inductive Voronoi graph; where said Voronoi graph can be a complete or partial graph, a classical Voronoi diagram, or a more general Voronoi diagram with generalized, or relaxed Voronoi cell requirements such that the only determining factor is whether or not a point participating in the cell is closer to the generator for the cell than any other generator for the Voronoi diagram. These generalized Voronoi diagrams can contain cells that are polygonal, polytopal, or any other generalized geometric shape that can be used to bound a region. The data for said Voronoi diagrams can be any set of information, continuous or discrete, finite or uncountable infinite. A component of this invention relates to the automatic rigging of 3D computer models, route planning, and molecular medicine.

BACKGROUND OF THE INVENTION

Voronoi diagrams are a highly studied art due to their wide range of applicability to a diverse set of fields such as, but not limited to, molecular modeling, bio-informatics, robotic route planning, and computer graphics. The traditional Voronoi diagram V is defined as the partitioning of a plane P containing n points, or generators g, into n distinct polygons such that each polygon contains only a single generator g and that every point p inside of a polygon POLY is closer to the generator g for POLY than the generator g' for some other polygon POLY'. FIG. 1 shows a Voronoi diagram generated by a set of random points. In FIG. 1, 1 is a generator for the Voronoi cell 2.

Despite the amount of research that has been performed in the art of Voronoi diagram construction, it is still difficult to automatically construct Voronoi diagrams for complex generators and higher dimensional spaces. For example, the automatic construction of a Voronoi diagram for a set of line segments in 3D is still considered an open problem. One of the reasons for this is that the definition of a Voronoi diagram must first be relaxed before generators that are more complicated than a point can be considered. For example, if we extend to concept of a Voronoi diagram in 3D from that which is constructed from a set of points to something that can be constructed for a set of lines then we immediately face the problem that the faces for our Voronoi diagram over lines in 3D are no longer planer, and in fact have a curved nature, FIG. 2.

Various groups have tried to automatically generate Voronoi diagrams for line segments, some even in 3D; however, a casual inspection of the treatment of the line segment endpoints in these diagrams usually invalidates the claim that said generated diagrams are Voronoi diagrams. Similarly, Boada and his group created a method that approximates a Voronoi diagram for a variety of shapes, including line segments; however, a close inspection of the cells computed by Boada et. al.'s method shows that the cells generated by said method in fact does not meet the requirements for a Voronoi cell.

The deficiency of the methods presented in prior work is largely due to the relaxed treatment that said groups give to the definition of a Voronoi diagram. To some degree this is necessary. For example, while Voronoi diagrams for point sets in high dimensional space can be generalized via the use of polytopes instead of polygons, more complicated generators, such as line segments, do require a further generalization of our definition so as to accommodate curved faces 3. However, Boada et. al. and Held et. al. generalize the definition of a Voronoi diagram to the extent that they now allow generators to be associated with multiple Voronoi cells, Voronoi cells to be associated with multiple generators, and Voronoi cells that contain points that are closer to an alternative generator g' than the primary generator g. Clearly, this violates both the definition and spirit of a Voronoi diagram. For the methods presented here, we define a Voronoi diagram V to be a partitioning of a space, or data set, into a set C of cells $C_i$, called Voronoi cells, based upon a set G of generators; such that every point $p \in C_i$ is closer to the generator i for $C_i$ than any other generator j in G. In this definition, "closer" can be according to any distance measure. For example, but not limited to, one embodiment may use Euclidian distance to determine closeness; another embodiment might use the Manhattan distance; yet another method may use the Minkowski distance, and etc.

It should also be noted that Kim et. al. devised a computationally intensive method for utilizing Voronoi diagrams of spheres and sphero-cylinders for the analysis of biomolecules. However, they do not claim that their novel method includes the methodologies for the construction of a Voronoi diagram; where the method that they presented in their patent includes the description of a method for the construction of a Voronoi diagram of spheres and sphero-cylinders. FIG. 20 depicts two pairs of such sphero-cylinders. The first pair, 1000 and 1001, are sphero-cylinders with non-zero radii. The second pair of sphero-cylinders, 1003 and 1004, are sphero-cylinders with zero-valued radii.

This construction of Voronoi diagrams of sphero-cylinders is related to the construction of Voronoi diagram for a set of line segments, or sphero-cylinders with zero-value radii, 1003 and 1004; however, the methodology developed by Kim et al does not present a method for handling the intersection of two sphero-cylinders, or potentially the intersection of two line segments, at an endpoint, 1005. In fact, said method does not at all investigate or handle the intersections of complex generators. Since it is the intersection of generators that generally invalidates a proposed Voronoi diagram construction, Kim et. al. neglected to solve the most critical component of Voronoi diagram construction. For example, if a sphero-cylinder 1003 with radius equal to zero intersects another sphero-cylinder 1004 with radius equal to zero in such a way that one of the half-spheres for the first sphero-cylinder perfectly overlaps one of the half-spheres for the other sphero-cylinder 1005 then the method presented by Kim et. al. will not be able to discriminate between points, 1006 and 1007, near said overlapping half-spheres that belong to the first sphero-cylinder, 1006 to 1003, from points that belong to the second sphero-cylinder, 1007 to 1004.

SUMMARY OF INVENTION

This Summary is not intended to limit the scope of the claimed subject matter or identify key or essential features of the claimed subject matter. This Summary is only provides, in an abridged form, a selection of concepts that are further described in the Detailed Description.

With the previous paragraph in mind, this disclosure details two novel methods for the derivation of Voronoi diagrams for a set of generators of arbitrary dimensionality and arbitrary complexity. The first novel method involves the construction of a Voronoi diagram via an intermediary mathematical game played over the input set of generators along with a finite input set of data values. This initial method is best suited for, but not limited to, applications where it is desirable to compute a mapping of a finite number of input data values to a finite number of input value-generator pairs (d, g); where such a pair would indicate that a given input d is closest to the given generator g. The second novel method involves the construction of a Voronoi diagram over an input set of generators alone. This second method is best suited for, but not limited to, applications where it is desirable to compute a set of equations that define the Voronoi diagram, and each component, or cell/Voronoi polygon, of the Voronoi diagram, so as to be able to arbitrarily select any given cell from the output and obtain a mathematical description for the selected cell.

The construction of such Voronoi diagrams has a diverse set of applicable uses. Here, we will present one such use. Specifically, we will present the use of Voronoi diagram constructed via the first novel method for the purpose of automatically segmenting, rigging, and then subsequently animating an input model. This automatic-rigging use-case is in itself a novel method for automatic rigging. The embodiment of the use case presented here is in no way meant to limit the potential use, or application, for Voronoi diagrams constructed using the following methods. On the contrary, the vast number of uses is so numerous and diverse that it would be impractical to list all of such uses here. As such, the automatic rigging use case shown here is to be interpreted as a non-limiting, illustrative use case scenario.

In addition to the novelty of the automatic-rigging method presented here, said method also utilizes a novel method for referencing the closeness of a point that participates in a joint to the remainder of the limb; or conversely, the center of the joint. This novel method for recording, referencing, or otherwise relating, a point in a model to the center of a joint is useful during the animation process for more fine controlled animations at the joints.

The scope of this claim is not in any way intended to be limited according to the structure or format of the input data, or the medium for implementation of the methods presented here. The methods described here are typically, but not necessarily, implemented on a computational device of some manner that is capable of receiving, or loading, input data in such a manner as to enable the execution of the aforementioned methods.

BRIEF DESCRIPTION OF THE DRAWINGS

Similarly numbered elements in the attached drawings correspond to one another.

FIG. 6 depicts a non-limiting example of a normal form game 100 and the associated extensive form 101 for 100.

FIG. 7 depicts a non-limiting example of a normal form 102 game specification for a Voronoi diagram defined over the finite data set {p} with respect to the set {i, j} of generators.

FIG. 8 depicts some of the geometrical properties for a set S of generators containing line segments.

FIG. 22 depicts a method for segmenting data points near the intersection of two line segment generators.

DETAILED DESCRIPTION

Figure 1:
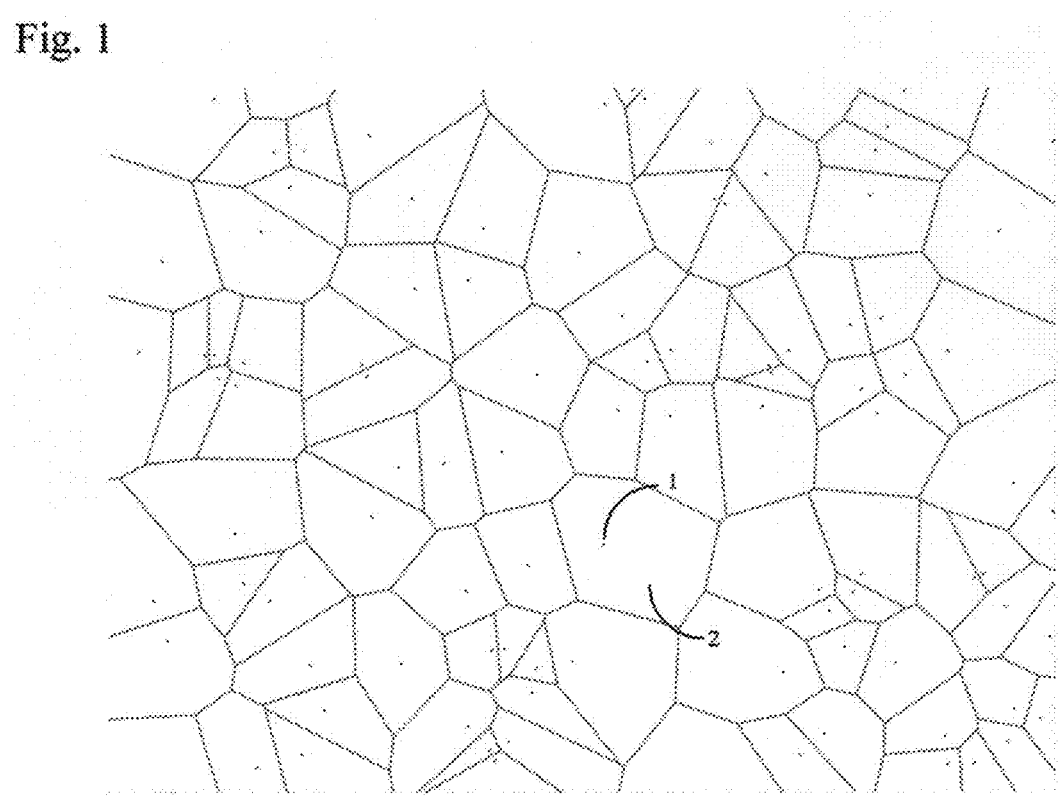
FIG. 1 depicts an example Voronoi diagram for a set of input point generators.
Figure 2:
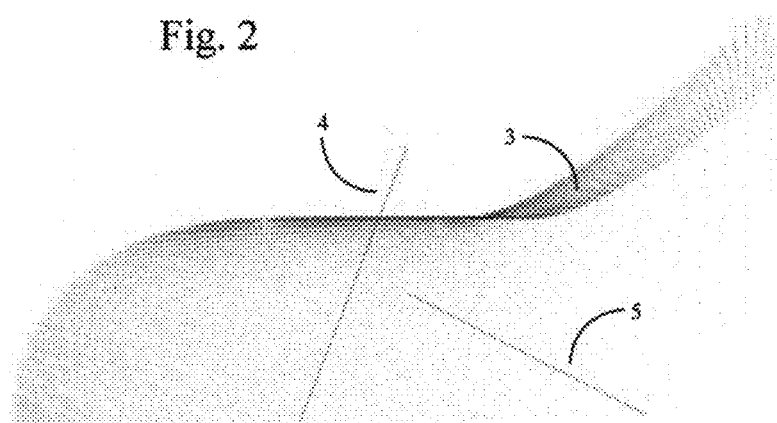
FIG. 2 depicts an example curved-face 3 for two, adjoining Voronoi cells in a Voronoi diagram of two lines. The Voronoi Diagram in FIG. 2 was computed for a unit cube; thereby truncating the lines, 4 and 5, and face 3 at the boundaries for said unit cube. As such, 3, 4, and 5 are to be interpreted as unbounded, and extending, beyond the unit cube, to an infinite length in a direction that is appropriate for the portions of 3, 4, and 5 shown in FIG. 2.
Figure 3:
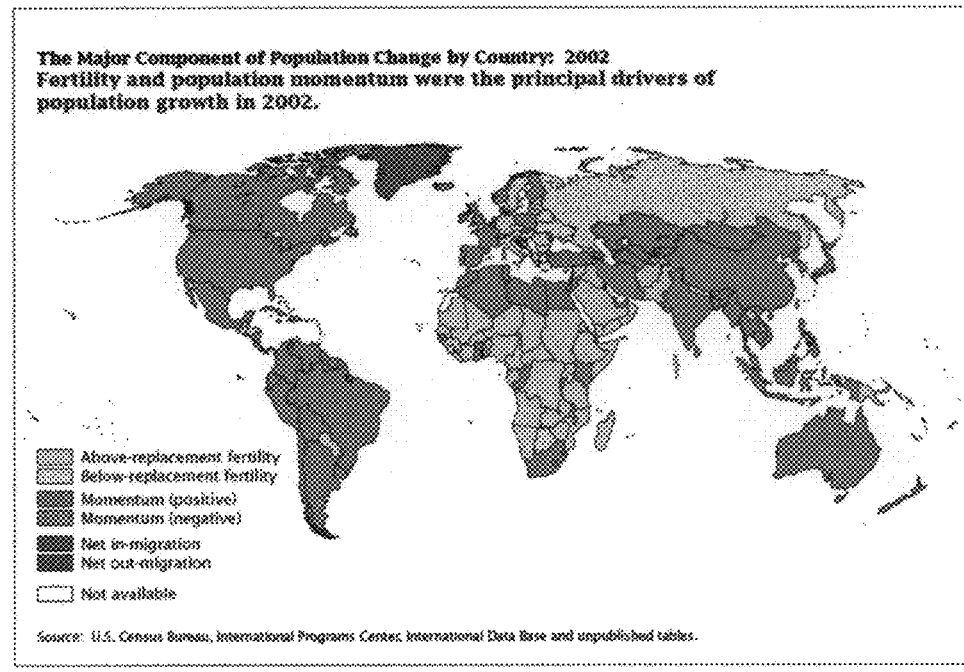
FIG. 3 depicts an example discrete, discontinuous data set. The data figure shown in FIG. 3 was taken from the US Census Bureau's 2002 report on Global Population Growth.

The presented disclosure is directed at the derivation of a Voronoi diagram, Voronoi-like diagram, Voronoi partitioning, and/or Voronoi-like partitioning of an input set of information, mathematical space, or information, which we will from hence forth on refer to as data, for the purpose of analyzing data, or data space, for the purpose of analyzing a space, so as to formulate conclusions, and/or predictions, with regards to the presented data, or data space. An example data space is a unit cube within which the Voronoi diagram was computed in FIG. 2. An example data set, or set of discrete information, is shown in FIG. 3. The data, data set, presented in FIG. 2, FIG. 3, are meant to serve as a non-limiting example of a potential data space, data set.

Figure 4:
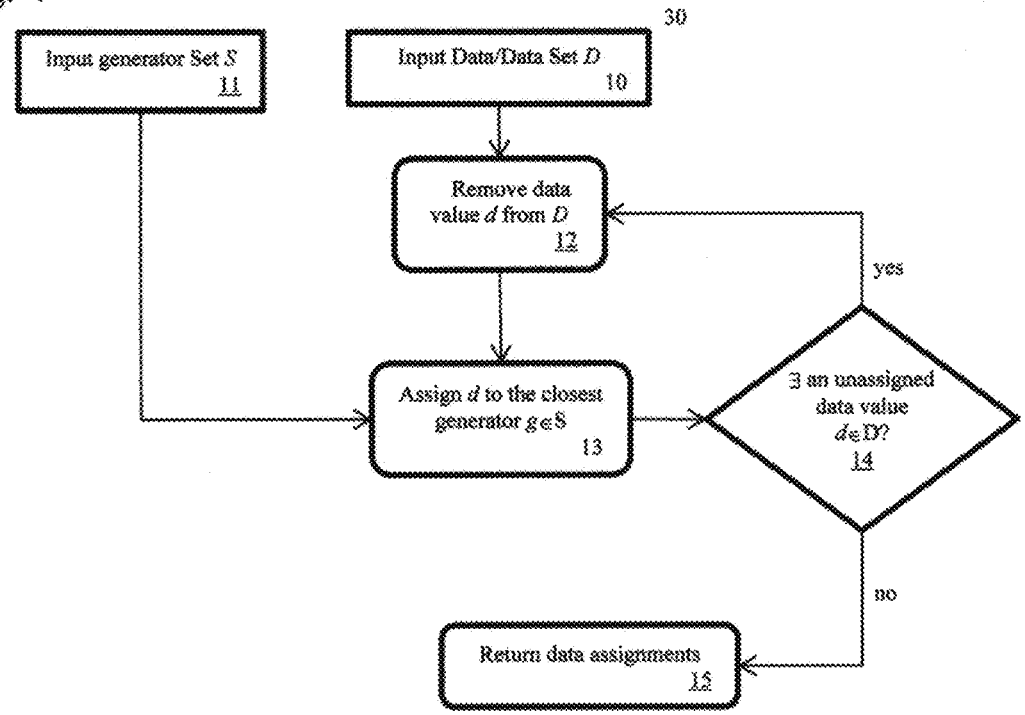
FIG. 4 depicts a high level perspective of the process for the first novel method, 30, for creating a Voronoi diagram.

FIG. 4 depicts a high level perspective of the first method for the derivation of a Voronoi diagram over a data space or input data set. 30 is the high level method in FIG. 4. The method presented in FIG. 4 is optimally applied to finite, discrete input data sets, but not limited in application to finite, discrete input data sets. If the input data set 10 is finite, then the method presented in FIG. 4 can be said to induce a Voronoi partitioning of 10 according to the supplied set of generators 11. If the input data set 10 is non-finite, or infinite, then the embodiment presented in FIG. 4 can be said to induce a Voronoi partitioning of the data space for 10, where the subsequent Voronoi diagram graphic, or visualization, can be generated as in the high level method presented in FIG. 5.

10 and 11 in the embodiment shown in FIG. 4 are the input data/data space/data set D and the input generator set S, respectively. The data in 10 can be any form of information, including the mathematical space over which S itself is defined. S is a set of generators g; where g is any, and not limited to, geometrical, or non-geometrical, object which can be related to D via mathematical means. 13 in FIG. 4 utilizes a mathematical game to determine which generator g the input data valued is closest to; and therefore should be assigned. Step 14 in FIG. 4 cycles back to Step 12 until all data values have been evaluated; upon which time the partitioned data is returned in Step 15. Said partitioned data can then be passed to the method presented in FIG. 5 to be subsequently converted into a Voronoi diagram. The process outlined in FIG. 5 sequentially searches the data values partitioned in 13 to determine if two neighboring values are assigned to different generators. If they are, then we know that we have detected a face and pass said face-values to Step 22. Step 22 collates the face-values and then tessellates, or simply passes the values, as in FIG. 11, FIG. 12, FIG. 13, and FIG. 14, in step 23 to a subsequent process in a format that is able to be rendered to an output device. The embodiment of the method in FIG. 4 is not meant to be interpreted as limiting with regard to any reasonable modification of the method that still retains the key concepts presented in the method. For example, and equivalent, yet different embodiment for the method presented in FIG. 4 would be to retrieve a set d of data values d in 12, and independently, but concurrently assign each value d∈d to a generator in 13 instead of the sequential approach presented in FIG. 4. Another alternative embodiment would be to assign all data values concurrently. Alternatively, another embodiment may be to add values to a queue, and then continue with the data assignment process until the queue is empty. Again, another embodiment may be to just remove values from D for assignment until D is empty.

The assignment performed in 13 is determined via the use of a mathematical game. Note: while the embodiment presented here utilizes a mathematical game, this is not meant to be limiting, and is to be interpreted as the use of any mathematical equivalent of a mathematical game. For example, another embodiment may be to use the linear programing equivalent of the game that is played during step 13. We may refer to the mathematical game in 13 of FIG. 4 henceforth as either mathematical game, normal form game, extensive form game, or just game; where the distinctions between normal form and extensive form games is apparent to anyone familiar to the art. FIG. 6 demonstrates a non-limiting example of such a mathematical game for 13. The game 100 in FIG. 6 is the normal form of the classical prisoner's dilemma game: which is well known to anyone that is familiar with the art and discipline of game theory. 101 in FIG. 6 is the extensive form of the same classical prisoner's dilemma game as in 100. We can define both 100 and 101 according to the triple <N, A, u>: where N is the set of n players; $A=A_1 \times \ldots \times A_n$, where $A_i$ is the finite set of actions for player i; and $u_1, \ldots, u_n$), where $u_i: A \rightarrow \mathcal{R}$ is the utility function. Where said mathematical definition of a triple for a mathematical game is common knowledge to those who are familiar with the art of game theory. Additionally, said mathematical definition for 100 and 101 is identical because both 100 and 101 are instances of the prisoner's dilemma problem; where the prisoner's dilemma problem is also known to those that are familiar with the art of game theory.

Figure 5:
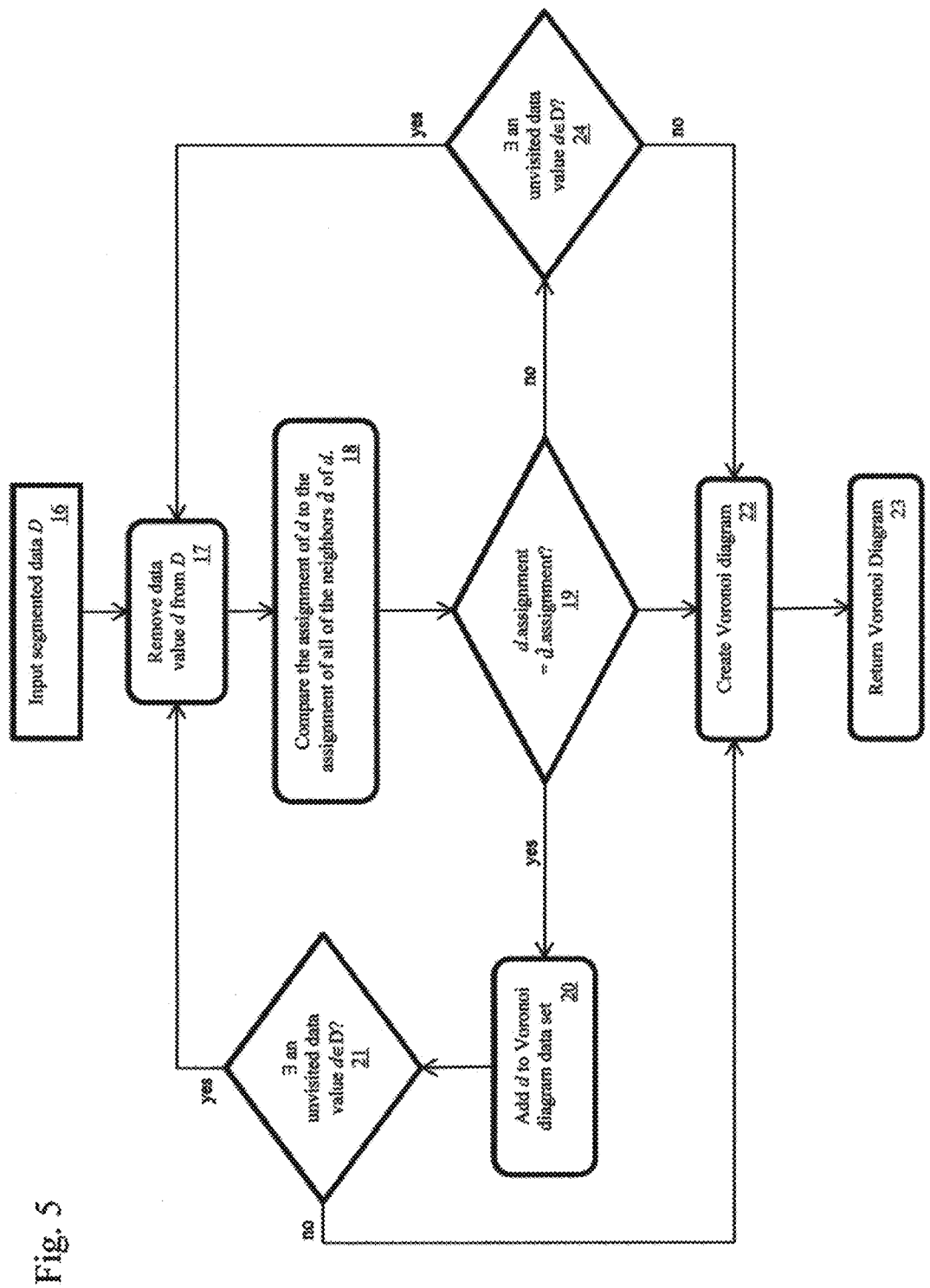
FIG. 5 depicts a high level perspective of one possible process for generating a Voronoi diagram graphic from the partitioned data generated by the process presented in FIG. 4.

A non-limiting example for the game played during the decision process of step 13 in FIG. 5 is presented in FIG. 7. The mathematical definition for the game in FIG. 7 can be regarded as the same as was stated for 100 and 101 with the exception that the actions will be the assignment of the input data point 107 to one of the line segments, 108 or 109, in 103, and with the exception that the utilities for said assignment-actions be based upon the utility of the available assignments. The embodiment presented in FIG. 7 is only to be interpreted as one possible example for the game performed during 13: and not in any way to be interpreted as limiting or exhaustive. For example, another embodiment could have ten points and one line segment. Another embodiment could have one thousand line segments and a million data points. Yet another embodiment could have one hundred thousand line segments and uncountably infinite data points: or be defined over a data space.

In FIG. 7, 104 and 105 are the players i and j for the game 102. 113 is the payoff, or utility, to players 104 and 105. 106 is one possible action that may, but is not necessarily, performed by player 104; and where the action 106 is to be read as "assign input data point p to player j." The action set $A_i$ for each player i for 102 is defined over the set of all data-value-player pairs; such as the data-value-player pair 106. 103 is the non-limiting use case scenario over which 102 is defined. 110 is the set of generators S:={i, j}, where 108 is the generator i and 109 is the generator j. In the non-limiting embodiment presented in FIG. 7, both 108 and 109 are line segments such that 108 intersects 109 at a common endpoint, or bound. 107 is the input data value p that constitutes the entirety of the input data for the non-limiting embodiment presented in 103 in FIG. 7. 112 is the mathematical projection of 107 onto 109. 111 is the mathematical projection of 107 onto 108. The utilities, 113, 114, 115, and 116, for the actions for 102 are computed using a distance function d(i p); where i is a player, such as 104 or 105, and p is an input data value, such as 107.

The distance function d(i, p) can be derived using any distance measure, such as, but not limited to, Euclidean distance, Manhattan distance, Minkowski distance, Chebyshev distance, Hamming distance, and Mahalanobis distance. In addition to a generic distance function, d(i, p) may, but does not necessarily, have generator specific logic. d(i, p) may, but does not necessarily, also have a set, or library, of decision process, functional methodologies, or computational process that are chosen from to respond to a varying number of generator types, varieties, or classifications. It is further possible that d(i, p) is itself the payoff for an encapsulated game that is played over a set of potential generators, or generator-generator interactions. Additionally, it is possible that d(i, p) is incorporated into the initial game structure 102 to form a more complicated game; such as, but not limited to, a Markov game or a Bayesian game. Note, the aforementioned description of d(i, p) in the embodiment presented here, as well as the subsequent examples for d(i, p), are in no way meant to be exhaustive or limiting with respect to the specification of d(i, p).

As a non-limiting example, consider a set S, for example 110, of line segments as the set of generators for a Voronoi diagram. FIG. 8 demonstrates some of the relevant geometric properties for sets of generators defined over line segments, such as 110. In FIG. 8, 220 shows the relationship between the α-value, 207, from the projective function for a data value, such as 107 in FIG. 7, onto a line segment, such as 108 in FIG. 7. 221 in FIG. 8 shows the geometrical properties associated with a system of line segments that intersect at a common bound.

In FIG. 8, 200 is the line over which the line segment 201 is defined. 201 is bound by the endpoints $\dot{p}$, 202, and $\ddot{p}$, 203. 204, 205, and 206 are potential data values, where the dotted lines in 220 indicate the projection $\text{proj}_{200}\{204|205|206\}$ of the data values 204, 205, and 206 onto the line 200. α in 220 is the α-value associated with said projective function. One embodiment for such a projection can be defined as:

$$\text{proj}_i p = \dot{p} + \alpha(\ddot{p} - \dot{p})$$

where α is defined as $$\alpha = \frac{(p - \dot{p}) \cdot (\ddot{p} - \dot{p})}{\|\ddot{p} - \dot{p}\|}.$$

The embodiment of the projective function presented here is meant to be non-limiting. For example, an alternative embodiment could be the projection onto a plane. Yet another embodiment could be the projection onto the surface of a sphere, or a cube. An additional embodiment could be the projection onto a polytope.

221 and FIG. 22 illustrates one possible, non-limiting method for determining which generator a data value should be assigned, or which generator a data value is "closest to," for the scenario of two line segments intersecting at a common bound 210. In 221, j, 208, and i, 209, are the line segments that define the set S of generators for the to-be-derived Voronoi diagram V. Alternatively, we could interpret the line segments shown in the embodiment presented in 221 as a subset of the total set S of generators for V. 210, $\dot{p}$, and 211, $\ddot{p}$ are the bounds on the line segment 209. 210 is also a common bound for 208 and 209: meaning that 208 and 209 intersect at 210. 213 is the hyperplane H that bisects the angle between 208 and 209, see 2003. 212, p, is the data value that must be assigned to either 208 or 209 depending on whether 212 is "closer" to 208 or 209, see 2007, 2010, and 2011. 214, θ, is the angle between 209 and 213, see 2004. 215 is the angle between (p–$\dot{p}$) and 209, see 2005. By "angle between" we are to be understood as referring to the angle between H and the plane defined over the line that passes through the normal to the plane defined by 208 and 209 and the line that passes through 209, or (p–$\dot{p}$), respectively.

For the non-limiting example set S={i, j} of generators i and j from 103, the utility function for 102 can be defined over the action profile $a_i:=(a_{i,1}i, \ldots, a_{i,k})$, where $k=|a_i|$, for a given player, or generator, i as:

$$u_i(a_i) = \Sigma_{a_{i,v} \in a_i} u_i(a_{i,p})$$

where the sub-function $u_i(a_{i,p})$ is defined as:

$$u_i(a_{i,p}) = \begin{cases} 1 & d(i, p) = \min\{d(j, p) \mid j \in S\} \\ 0 & \text{otherwise} \end{cases},$$

and where d(i, p) is defined as:

$$d(i, p) = \begin{cases} \|p - \text{proj}_i p\| & \text{if } 0 < \alpha < 1 \\ d_{\dot{p}}(i, p) & \alpha < 0 \\ d_{\ddot{p}}(i, p) & \alpha > 1 \end{cases}.$$

Using the geometric properties presented in 221, the sub-function $d_{\dot{p}}(i, p)$ is defined as:

$$d_{\dot{p}}(i, p) = \begin{cases} \|\dot{p} - p\| & \text{if } \deg(\dot{p}) = 1 \\ \|\dot{p} - p\| & \deg(\dot{p}) > 1 \wedge \phi(\dot{p}) < \theta(\dot{p}), \\ \infty & \text{otherwise} \end{cases}$$

where deg($\dot{p}$) is the number of generators that intersect at the point $\dot{p}$, see 2006 and 2009 in FIG. 22. $d_{\ddot{p}}(i,p)$ is defined the same as $d_{\dot{p}}(i, p)$, but with respect to $\ddot{p}$ instead of $\dot{p}$, see 2006 and 2009 in FIG. 22, $$d_{\ddot{p}}(i, p) = \begin{cases} \|\ddot{p} - p\| & \text{if } \deg(\ddot{p}) = 1 \\ \|\ddot{p} - p\| & \deg(\ddot{p}) > 1 \wedge \phi(\ddot{p}) < \theta(\ddot{p}). \\ \infty & \text{otherwise} \end{cases}$$

The embodiment presented in 221 is not to be interpreted as limiting. The method presented here is to be interpreted as any utilization of the geometrical properties presented in 221 for the purpose of segmentation.

Figure 9:
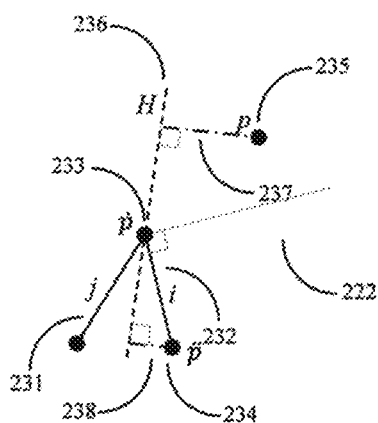
FIG. 9 presents additional geometrical properties for a set S of generators containing line segments that can be used for an alternative generator intersection resolution method.

For example, an alternative embodiment of the sub-functions $d_{\dot{p}}(i, p)$ and $d_{\ddot{p}}(i, p)$ can be defined utilizing the alternative interpretation, shown in FIG. 9, of the geometrical properties shown in 221. 222 in FIG. 9 presents the additional geometrical information which can be used to determine which generator, 231 or 232, a data value 235 is "closest to" for the scenario where 231 and 232 intersect at a common bound 233. In FIG. 9, 237 indicates the projection of 235 onto the hyperplane 236 that bisects the angle between generators 231 and 232, and 238 indicates the projection of 234 onto 236. With this geometrical information, we can redefine $d_{\dot{p}}(i, p)$ and $d_{\ddot{p}}(i, p)$ as:

$$d_p(i, p) = \begin{cases} \|p - \bar{p}\| & \text{if sign}(proj_H p) = \text{sign}(proj_H \bar{p}) \\ \infty & \text{otherwise} \end{cases},$$

and $d_{\bar{p}}(i, p)$ can be defined as:

$$d_{\bar{p}}(i, p) = \begin{cases} \|p - \bar{p}\| & \text{if sign}(proj_H p) = \text{sign}(proj_H \bar{p}) \\ \infty & \text{otherwise} \end{cases}.$$

Note that the definitions for $d(i, j)$, $d_p(i, p)$, and $d_{\bar{p}}(i, p)$ are non-limiting, and are only meant to be an explanatory example of the mathematical properties used during assignment in 13, and as one particular, non-limiting, form of the functions $d(i, j)$, $d_p(i, p)$, and $d_{\bar{p}}(i, p)$ that are necessary to compute the Voronoi diagram for a general set of generators. It should also be noted that the example forms for the functions $d(i, j)$, $d_p(i, p)$, and $d_{\bar{p}}(i, p)$ presented here are use case specific to a set of line segment generators. This said, it should be evident to anyone familiar with the art that a prohibitively large set of varieties for the functions $d(i, j)$, $d_p(i, p)$, and $d_{\bar{p}}(i, p)$ will be necessary to fully accommodate here all geometric forms that may be used as generators.

Figure 10:
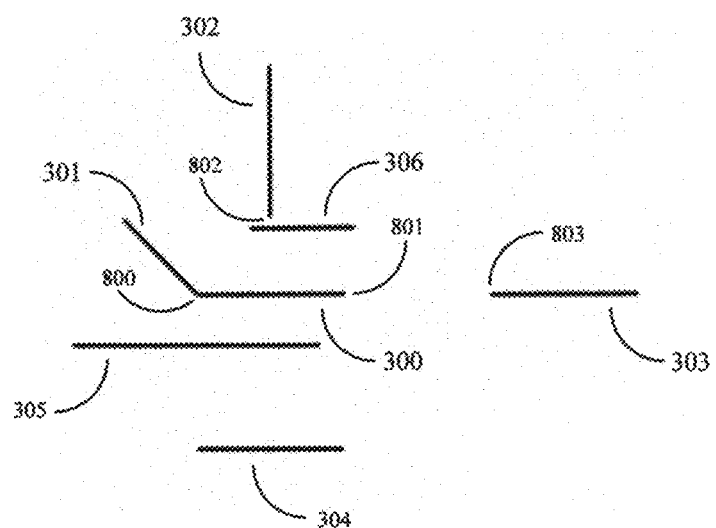
FIG. 10 shows an example set S of line segment generators for a Voronoi diagram.
Figure 11:
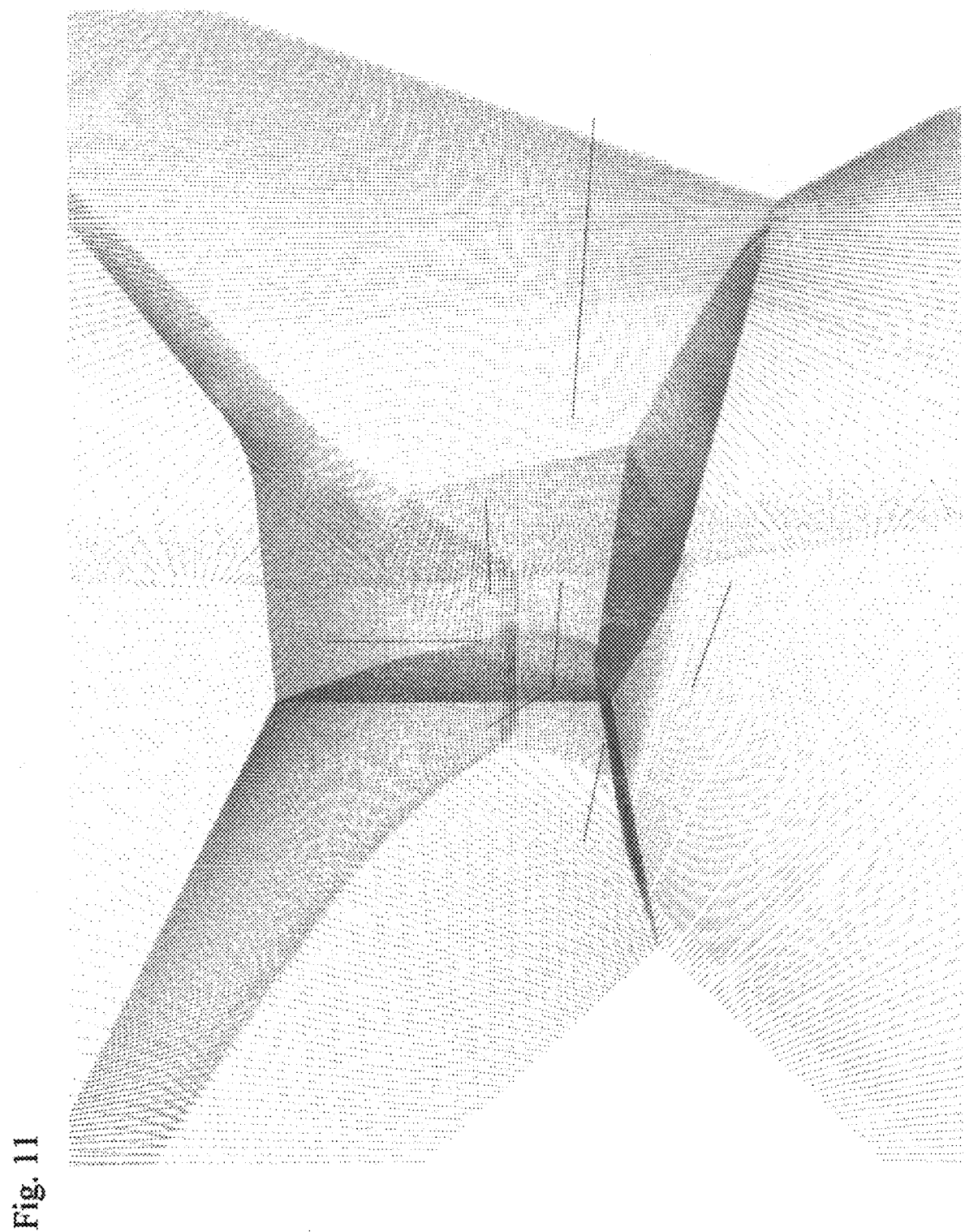
FIG. 11 shows the Voronoi diagram computed for the set S of line segment generators from FIG. 10.
Figure 12:
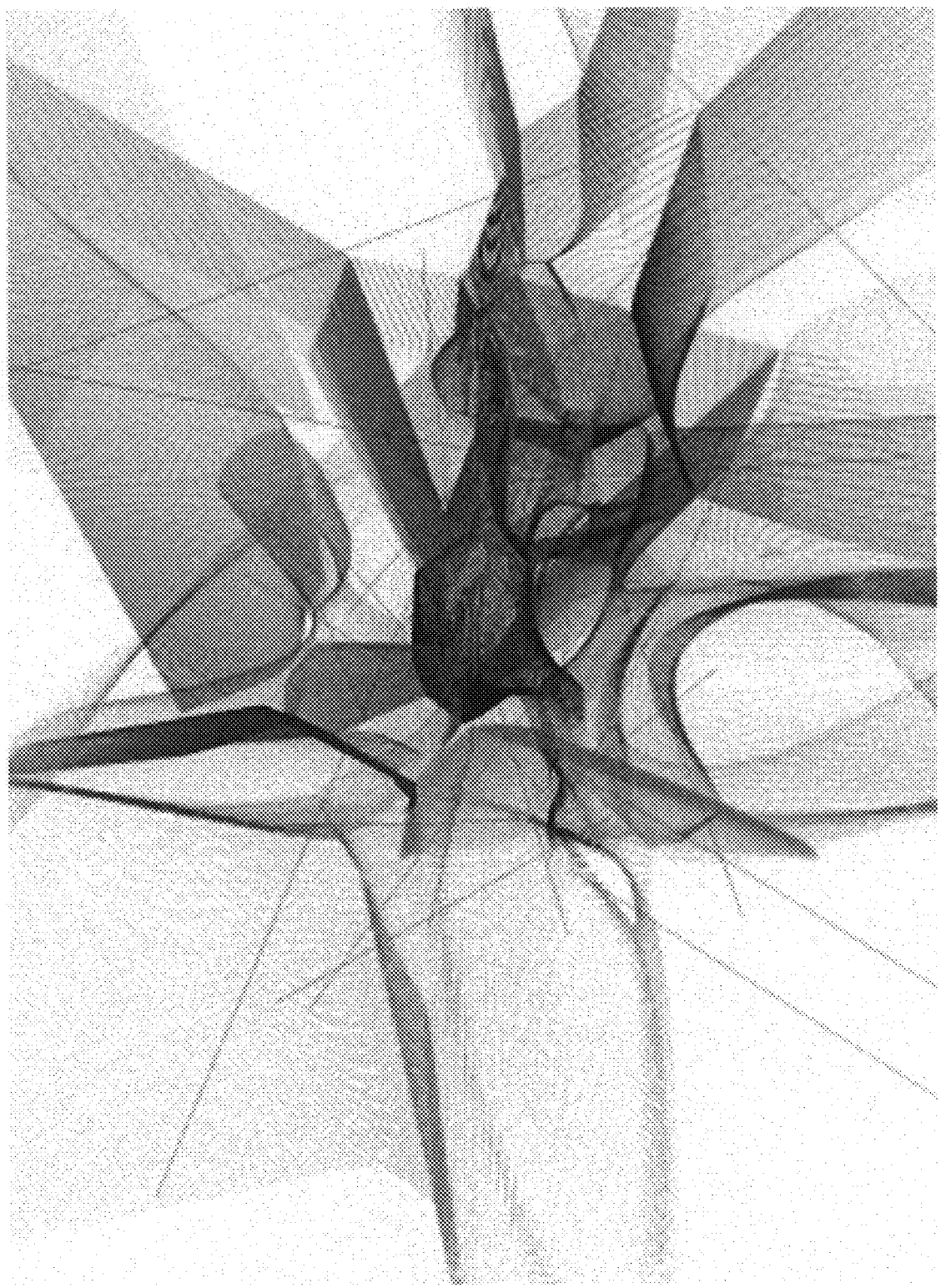
FIG. 12 shows a Voronoi diagram computed for a set S of 25 random line segment generators using 30.
Figure 13:
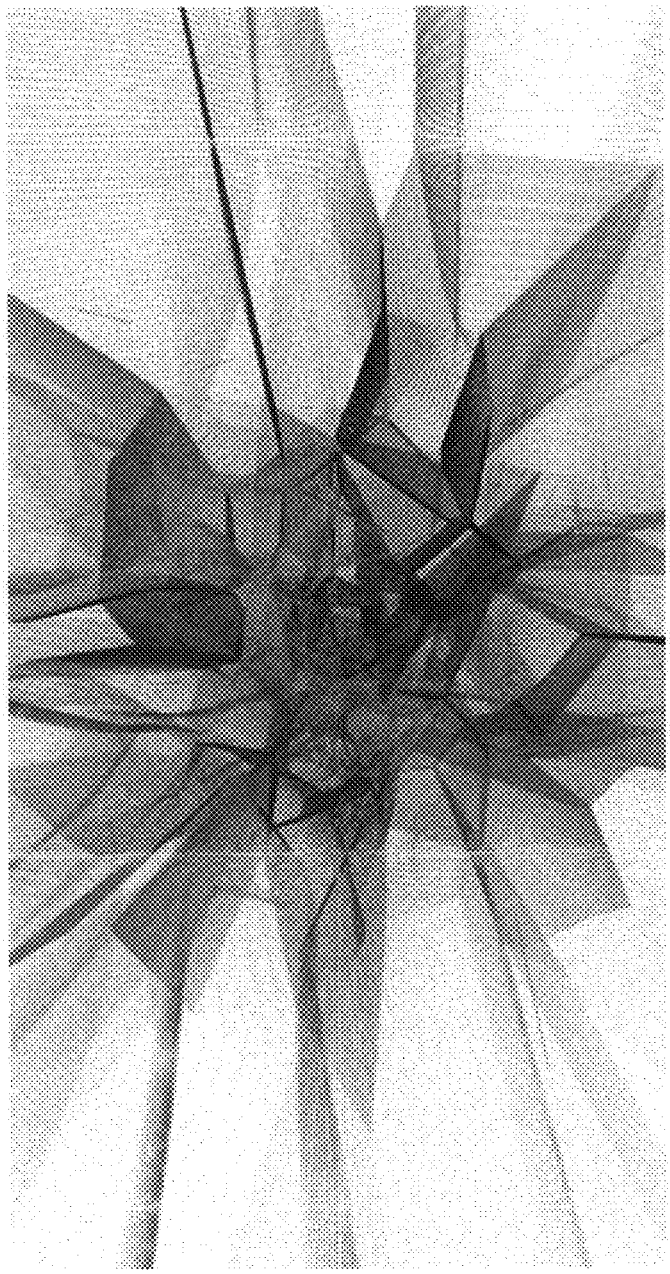
FIG. 13 shows a Voronoi diagram computed for a set S of 100 random line segment generators using 30.
Figure 14:
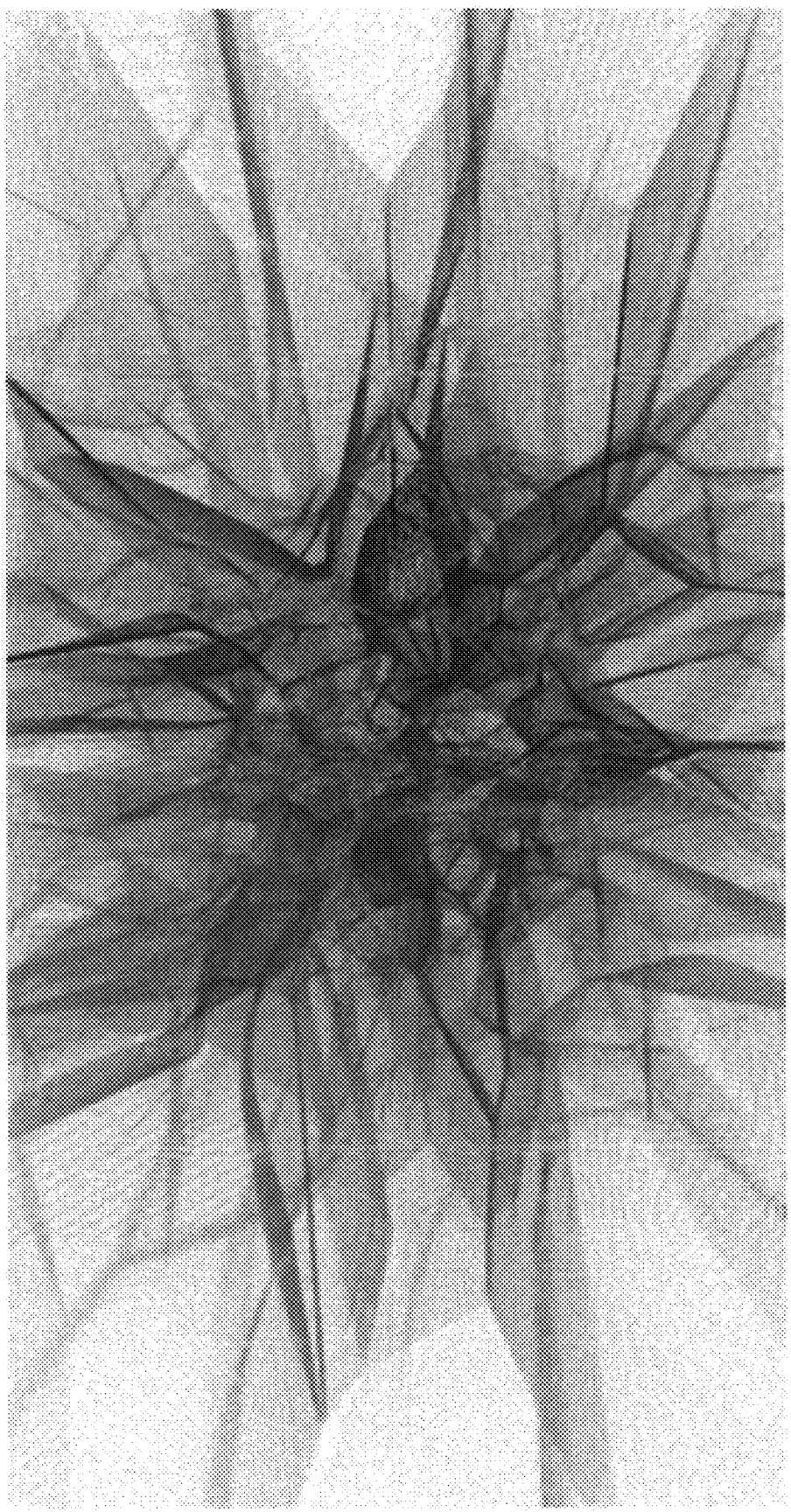
FIG. 14 shows a Voronoi diagram computed for a set S of 250 random line segment generators using 30.

FIG. 11, FIG. 12, FIG. 13, and FIG. 14 show examples of Voronoi diagrams computed using a game, such as 102 in FIG. 7. The Voronoi diagram shown in FIG. 11 was computed for the set S of generators {300, 301, 302, 303, 304, 305, 306} shown in FIG. 10. FIG. 12 was generated with respect to a random set of 25 random line segments. FIG. 13 was generated with respect to a random set of 100 random line segments. FIG. 14 was generated with respect to a random set of 250 random line segments. The lengths of the line segments in FIG. 12 were unrestricted. The lengths of the line segments in FIG. 13 and FIG. 14 were restricted to a maximum length of 2500 units.

Figure 15:
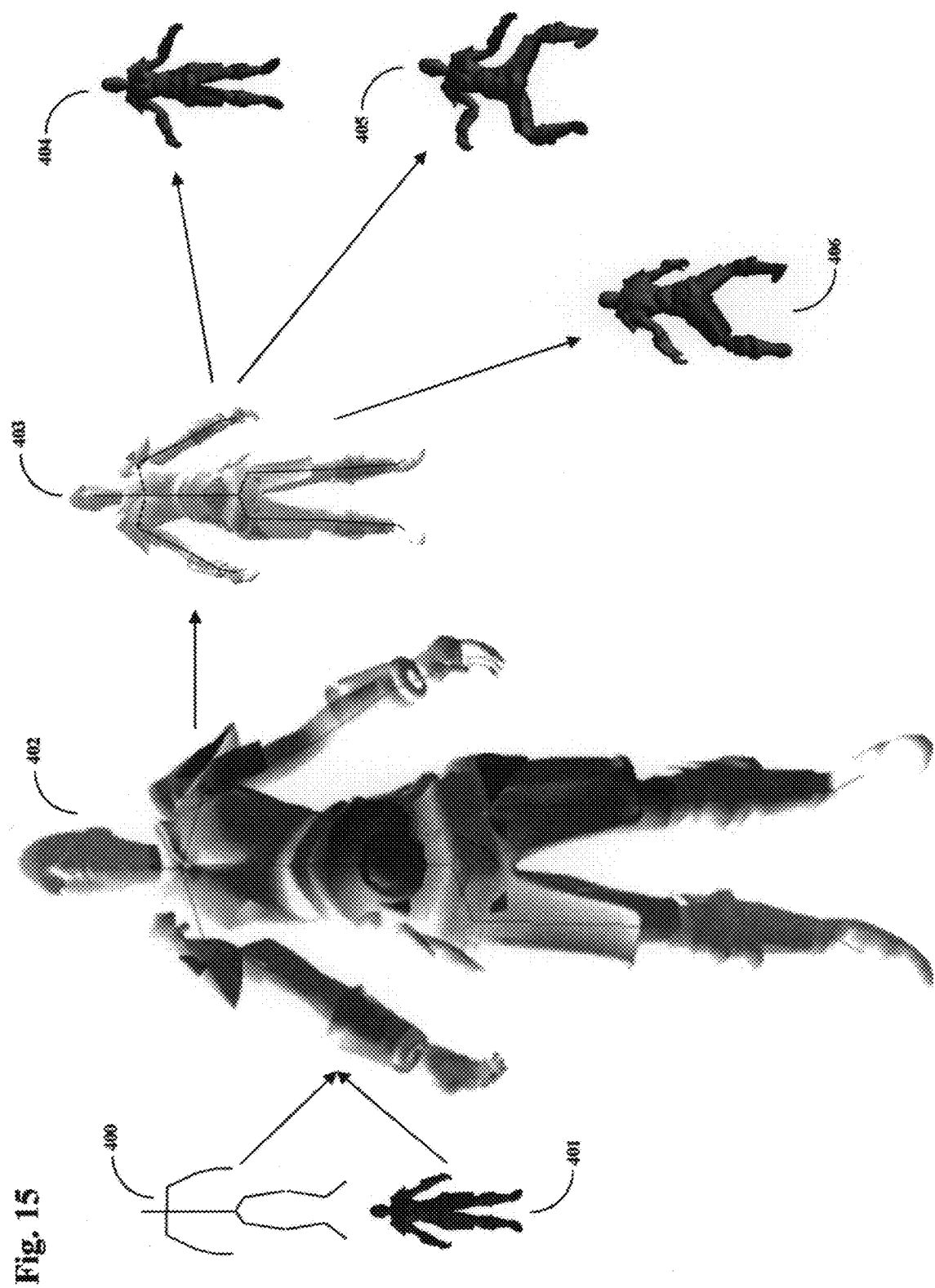
FIG. 15 details an example process by which a model is automatically rigged to an animation skeleton and then subsequently animated.

While the method presented in FIG. 4, which uses a game such as 102 in FIG. 7 to compute the Voronoi diagram for an input data set, utilizes a brute force approach, there are applications for Voronoi diagrams that cannot avoid the runtime requirements for such a brute force approach. For example, the automatic rigging of a graphical model, or just model, to an animation skeleton, or skeleton, requires the visitation of each vertex in the model at least once, if for no other reason then, to assign a bone weight to each vertex, see FIG. 15. FIG. 15 shows the process by which a Voronoi partitioning of an input model, 400, can be utilized for the process of automatically rigging 400 to an input animation skeleton, 401. 402 in FIG. 15 shows the Voronoi partitioning of 401 based upon 400; where each bone in 400 is viewed as a separate generator for 402. 403 is the final rigged model, where the joints for 400 are centered in the planes of separation between the two, or more, neighboring Voronoi cells in 402. 404, 405, and 406 represent three separate animations that are then subsequently applied to 403 via 400 using standard animation methods. Since a bone weight must be assigned to each vertex in 401 in order for 401 to be animated via 400 the brute force approach of the method presented in FIG. 4 is only marginally more costly than the process of assigning a known set of bone weights to 401.

Note, the embodiment of the automatic rigging example presented in FIG. 15 is a non-limiting example of an application for the method presented in FIG. 4. FIG. 15 is to be understood as being presented for illustrative purposes only, and not as a totality of potential uses for the method presented in FIG. 4. The method for the automated rigging procedure demonstrated in FIG. 15 is discussed in FIG. 21.

Figure 16:
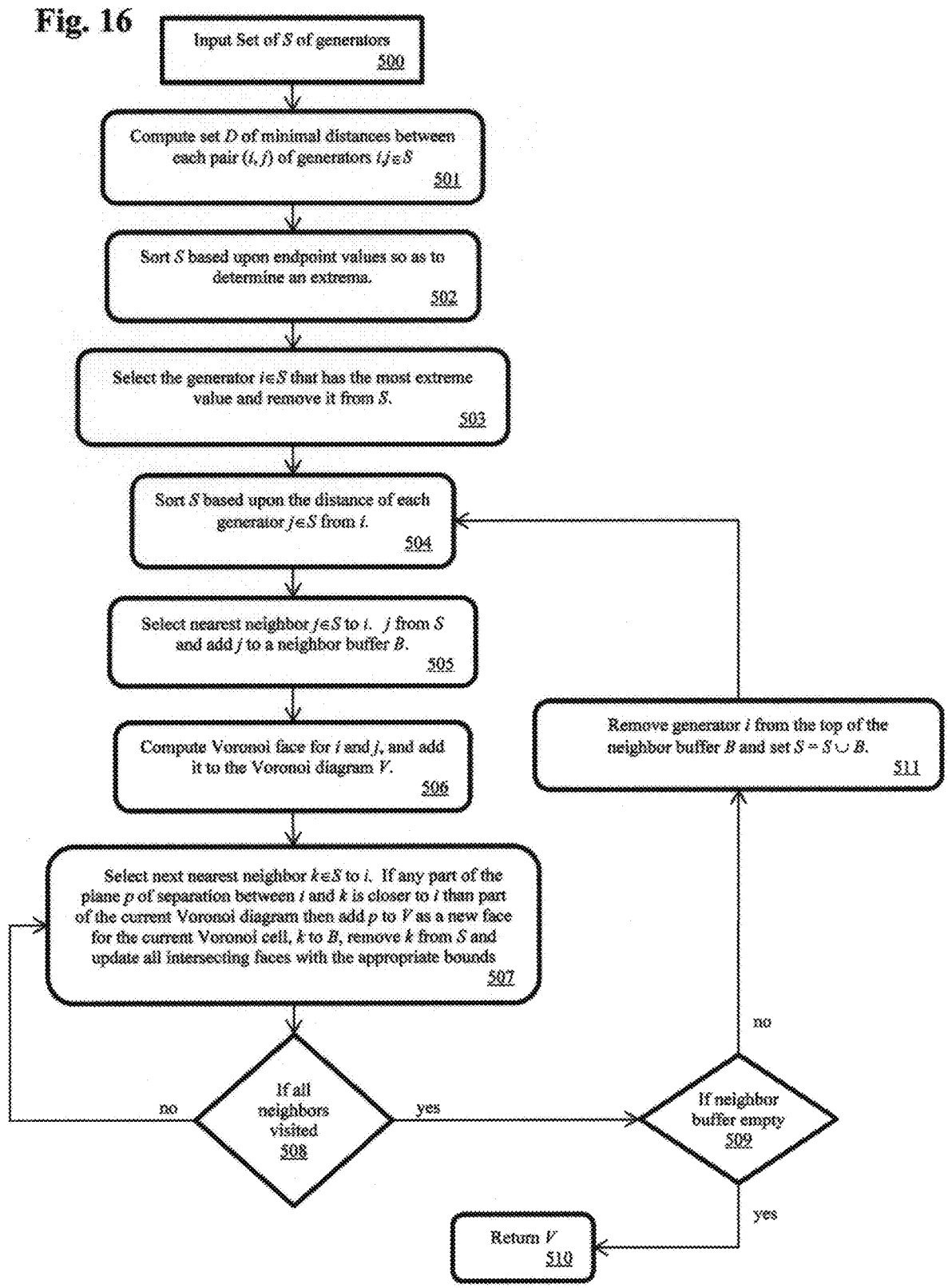
FIG. 16 details a high level perspective of a novel method for the derivation of a Voronoi diagram over a generic set of generators.

FIG. 16 details a high level perspective of a novel method for the derivation of a Voronoi diagram over a set of generators, of any form, via the direct derivation of equations for the facial specification of the Voronoi diagram: where a Voronoi diagram is composed of a finite set of Voronoi cells, which are in turn composed of a finite set of faces. Note: the high level perspective, or embodiment, presented in FIG. 16 is not intended to be interpreted as exclusive, strict, or rigid. Any practitioner in the art of algorithm design is familiar with the observation that most algorithms can be altered in many ways while still maintaining the functionality of the embodiment or implemented method. For example, another embodiment would be where 501 in FIG. 16 is moved after 503 without affecting the intent, purpose, methodology, or outcome of the method presented in FIG. 16. As such, the method presented in FIG. 16 is only to be presented as an outline of one possible implementation, or embodiment, for the method discussed.

The input to the embodiment of the method presented in FIG. 16 is a set S of generators for the to-be-generated Voronoi diagram. In 501, the minimum distance between each pair $(i, j)$ of generators $i,j \in S$ is computed. It should be noted that any of a number of distance measures could be used in 501; including, but not limited to, Euclidean distance, Manhattan distance, or Hamming distance. This minimum distance can be derived utilizing any number of ways known to anyone familiar with the art. In Step 502 the generators in S are sorted so as to find a generator with an extreme value: such as, but not limited to, the generator i that has one of its endpoints being the farthest point in the +x direction. The generator i with an extrema from 502 is then selected in 503 and removed from S. In 504 the remaining generators in S are sorted according to their distance from i, as was computed in 501. The nearest neighbor j from 501 is then removed from S in 505 and added to a neighbor buffer B. The plane of separation between i and j is then computed in 506 and added to a set V, that will eventually become the Voronoi diagram for S, as a face for V.

In Step 507 the next closest neighbor k to i in S is checked to see if the plane p of separation between i and k contains a point closer to i than any of the points that participate in the current specification for the Voronoi cell $c_i$ for i. If there does exist such a point then p is added to V as a new face for $c_i$, and the current set of faces for $c_i$ are updated to reflect any bounds that are introduced by the inclusion of p in $c_i$. Next, k is removed from S and added to B.

In Step 508, the sorted list created in 504 is check to see if all generators $l \in S$ have been visited. If an unvisited generator k remains then we return to 507 and process k. If all neighbors have been visited, then we check to see if B is empty in 509. If B is empty then we return the derived Voronoi diagram for S in 510. If B is not empty then in 511 the nearest neighbor i is removed from the top of B and S is set to the union of S and B. i is then subsequently processed as before in Step 504.

Figure 17:
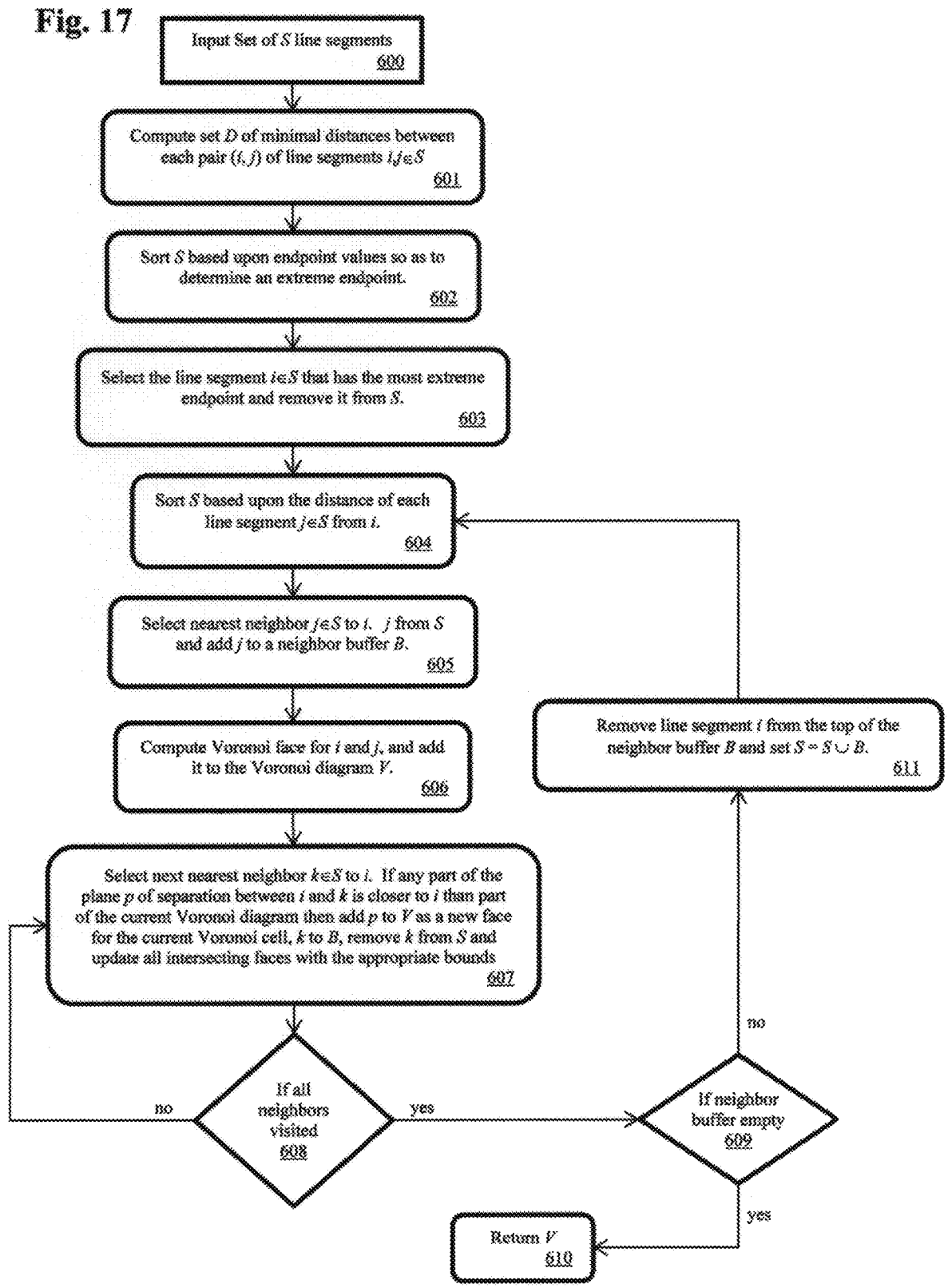
FIG. 17 details a high level perspective of a novel method for the derivation of a Voronoi diagram over a set of line segment generators.

FIG. 17 details a high level perspective of an application of the embodiment of the method in FIG. 16 for the derivation of a Voronoi diagram over a set of line segment generators via the direct derivation of equations for the facial specification of the Voronoi diagram. Neither the embodiment in FIG. 16 nor the embodiment in FIG. 17 are intended to be limiting. Many minor modifications can be made to the method presented in FIG. 16 and FIG. 17 while still retaining the spirit and intent of said method. For example, the embodiment in FIG. 17 is just a modification of the embodiment presented in FIG. 16. Similarly, and alternative embodiment could be constructed for spheres, or cylinders, or mixed generator sets of points, line segments, spheres, and etc. As such, the high level perspective presented in FIG. 17 is not intended to be interpreted as exclusive, strict, or rigid. Any practitioner in the art of algorithm design is familiar with the observation that most algorithms can be altered in many ways while still maintaining the functionality of the implemented method. As such, the method presented in FIG. 17 is only to be presented as an outline of one possible implementation for the method discussed.

The input to the embodiment of the method presented in FIG. 17 is a set S of line segments. In 601, the minimum distance between each pair (i, j) of line segments i,j∈S is computed. It should be noted that any of a number of distance measures could be used in 601; including, but not limited to, Euclidean distance, Manhattan distance, or Hamming distance. This minimum distance can be derived utilizing any number of ways known to anyone familiar with the art. In Step 602 the line segments in S are sorted so as to find a line segment with an extreme endpoint: such as, but not limited to, the line segment i that has one of its endpoints being the farthest point in the +x direction. The line segment i with an extreme endpoint from 602 is then selected in 603 and removed from S. In 604 the remaining line segments in S are sorted according to their distance from i, as was computed in 601. The nearest neighbor j from 601 is then removed from S in 605 and added to a neighbor buffer B. The plane of separation between i and j is then computed in 606 and added to a set V, that will eventually become the Voronoi diagram for S, as a face for V.

In Step 607 the next closest neighbor k to i in S is checked to see if the plane p of separation between i and k contains a point closer to i than any of the points that participate in the current specification for the Voronoi cell $c_i$ for i. If there does exist such a point then p is added to V as a new face for $c_i$, and the current set of faces for c, are update to reflect any bounds that are introduced by the inclusion of p in $c_i$. Next, k is removed from S and added to B.

In Step 608 the sorted list created in 604 is check to see if all line segments l∈S have been visited. If an unvisited line segment k remains then we return to 607 and process k. If all neighbors have been visited, then we check to see if B is empty in 609. If B is empty then we return the derived Voronoi diagram for S in 610. If B is not empty then in 611 the nearest neighbor i is removed from the top of B and S is set to the union of S and B. i is then subsequently processed as before in Step 604.

Note: the method presented in FIG. 17 is to be interpreted as a non-limiting example of how the method presented in FIG. 16 can be used to construct a Voronoi diagram. The line segment generators discussed in FIG. 17 are only one of an infinite number of possible generator classes. As such, the line segment application in FIG. 17 is to be viewed as only one possible version of the method presented in FIG. 16.

Figure 18:
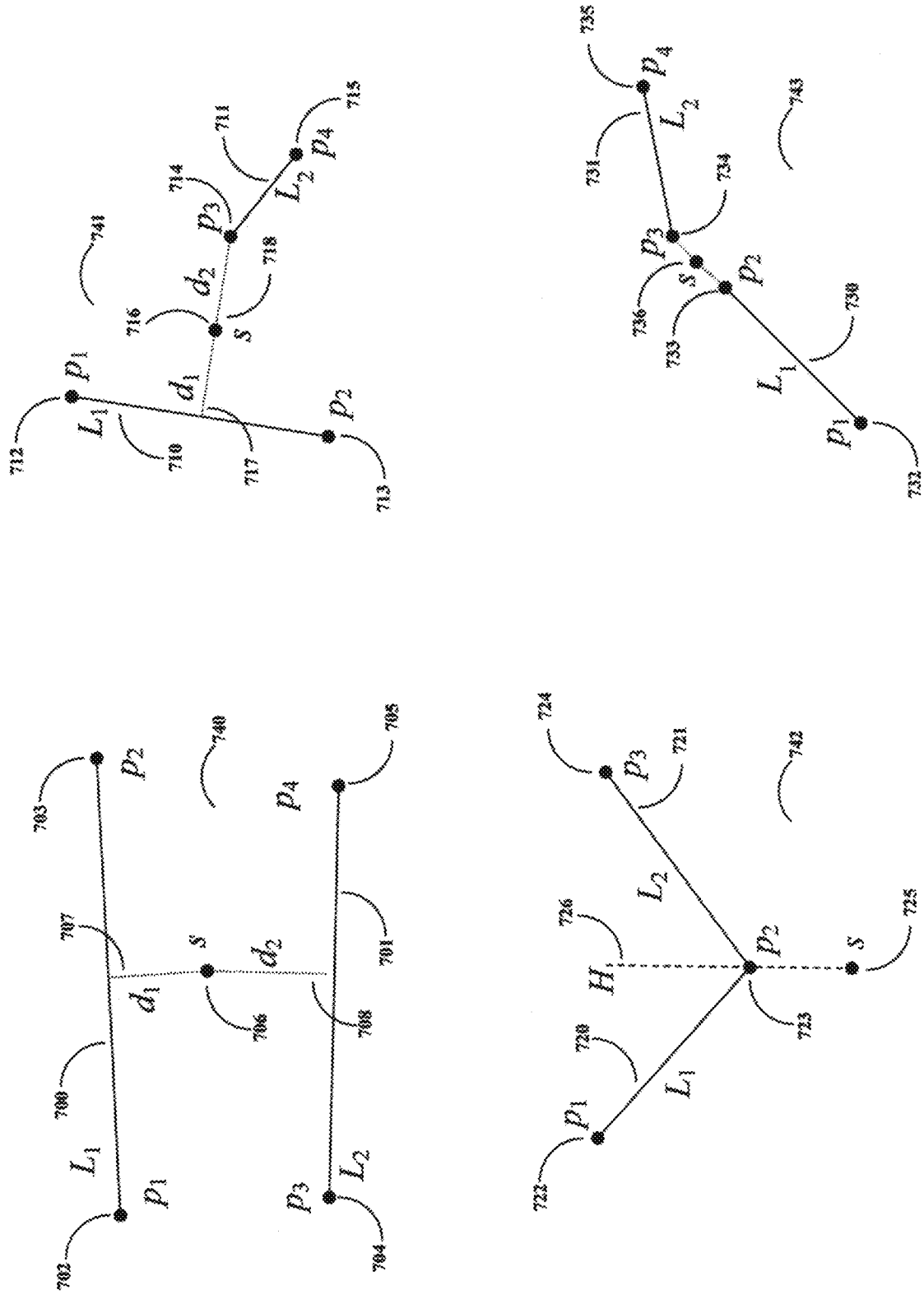
FIG. 18 shows four potential orientations for two line segments in three-dimensional space.

The Voronoi face computed in the embodiment presented in 606 is based upon one of the four scenarios in FIG. 18. The first scenario, 740, involves two line segments $L_1$ and $L_2$ such that no point p∈$L_1$ is closer to all points in $L_2$ than any other point p'∈i ∧ no point q∈$L_2$ is closer to all points in $L_1$ than some other point q'∈$L_2$. The second scenario, 741, involves two line segments $L_1$ and $L_2$ such that endpoint $p_3$ for $L_2$ is closer to all points p∈$L_1$ than any other point p'∈$L_2$. The third scenario, 742, involves two line segments $L_1$ and $L_2$ that intersect at a common bound 723. The fourth, and final, scenario, 743, involves two line segments such that endpoint $p_2$∈$L_1$ is closer to all off the points in $L_2$ than any other points p∈$L_1$ ∧ endpoint $p_3$∈$L_2$ than all points $L_1$ than any other point p''∈$L_2$.

For 740, 700 and 701 are the lines $L_1$ and $L_2$. 702 and 703 are the endpoints $p_1$ and $p_2$ for $L_1$. 704 and 705 are the endpoints $p_3$ and $p_4$ for $L_2$. 706 is a point s that is equidistant to $L_1$ and $L_2$. 707 is the perpendicular distance $d_1$ of 706 to 700. 708 is the perpendicular distance $d_2$ of 706 to 701. $d_1=d_2$. The equation for the plane of separation between 700 and 701 can be defined as:

$$f_F(s)=(s-\text{proj}_{L_1}s)\cdot(s-\text{proj}_{L_1}s)-(s-\text{proj}_{L_2}s)\cdot(s-\text{proj}_{L_2}s)=0.$$

For 741, 710 and 711 are the lines $L_1$ and $L_2$. 712 and 713 are the endpoints $p_1$ and $p_2$ for $L_1$. 714 and 715 are the endpoints $p_3$ and $p_4$ for $L_2$. 716 is a point s that is equidistant to $L_1$ and $L_2$. 717 is the perpendicular distance $d_1$ of 716 to 710. 718 is the distance $d_2$ of 716 to 714. $d_1=d_2$. The equation for the plane of separation between 710 and 711 can be defined as:

$$f_F(s)=(s-\text{proj}_{L_1}s)\cdot(s-\text{proj}_{L_1}s)-(s-p_2)\cdot(s-p_2)=0.$$

For 742, 720 and 721 are the lines $L_1$ and $L_2$. 722 and 723 are the endpoints $p_1$ and $p_2$ for $L_1$. 723 and 724 are the endpoints $p_2$ and $p_3$ for $L_2$: where $L_1$ and $L_2$ intersect at, or share, the common endpoint 723. 725 is a point s that is equidistant to $L_1$ and $L_2$. 726 is the bisecting hyperplane H that separates the points p' that belong to $L_1$ from the points p'' that belong to $L_2$. The equation for the plane of separation between 720 and 721 can be defined as:

$$f_F(s)=((\overline{L_2}\times\overline{L_1})\times(\overline{L_2}+\overline{L_1})\cdot(s-p_z)=0,$$

where $\overline{L_1}$ is the direction of the line segment L, away from the point of intersection 723.

For 743, 730 and 731 are the lines $L_1$ and $L_2$. 732 and 733 are the endpoints $p_1$ and $p_2$ for $L_1$. 734 and 735 are the endpoints $p_3$ and $p_4$ for $L_2$. 736 is a point s that is equidistant to $L_1$ and $L_2$. The equation for the plane of separation between 730 and 731 can be defined as:

$$f_F(s)=(s-p_2)\cdot(s-p_2)-(s-p_3)\cdot(s-p_3)=0.$$

As a non-limiting example of the application of the four scenarios 740, 741, 742, and 743, the Voronoi diagram V in FIG. 11 for the set S of generators in FIG. 10 can be define using the equations for the four scenarios 740, 741, 742, and 743 in FIG. 18 as follows. Looking at the Voronoi cell for 300, the back face for the Voronoi cell for 300 can be defined according to the equation:

$$f_{F_1}(s)=(s-\text{proj}_{L_{300}}s)\cdot(s-\text{proj}_{L_{300}}s)-(s-\text{proj}_{L_{306}}s)\cdot(s-\text{proj}_{L_{306}}s)=0,$$

where $$f_{F_1}(s)\leq(s-\text{proj}_{L_{300}}s)\cdot(s-\text{proj}_{L_{300}}s)-(s-p_{802})\cdot(s-p_{802}),$$

$$f_{F_1}(s)\geq(\overline{L_{301}}\times\overline{L_{300}})\times((\overline{L_{301}}\times\overline{L_{300}})-p_{800})\cdot(\text{proj}_H s-p_{800}),$$

$$f_{F_1}(s)\leq(s-p_{801})\cdot(s-p_{801})-(s-p_{803})\cdot(s-p_{803}),$$

$$f_{F_1}(s)\geq(s-\text{proj}_{L_{300}}s)\cdot(s-\text{proj}_{L_{300}}s)-(s-\text{proj}_{L_{304}}s)\cdot(s-\text{proj}_{L_{304}}s).$$

The remainder of the faces for V can be defined similarly to $F_1$. As a non-limiting example, the Voronoi cell for 300 can be defined as:

$$C_{300} = \bigcup_{w}^{F_{300}} f_{F_w}(s),$$

or more generally;

$$C_i = \bigcup_{w}^{F_i} f_{F_w}(s),$$

where $F_w \in F_i$, and $F_i$ is the set of faces for the generator i. The remainder of the cells for V can be defined similarly to $C_{300}$.

With the cells for V defined, V itself can be defined as:

$$V = \bigcup_{x}^{C} C_x,$$

where C is the set of cells for V.

Figure 19:
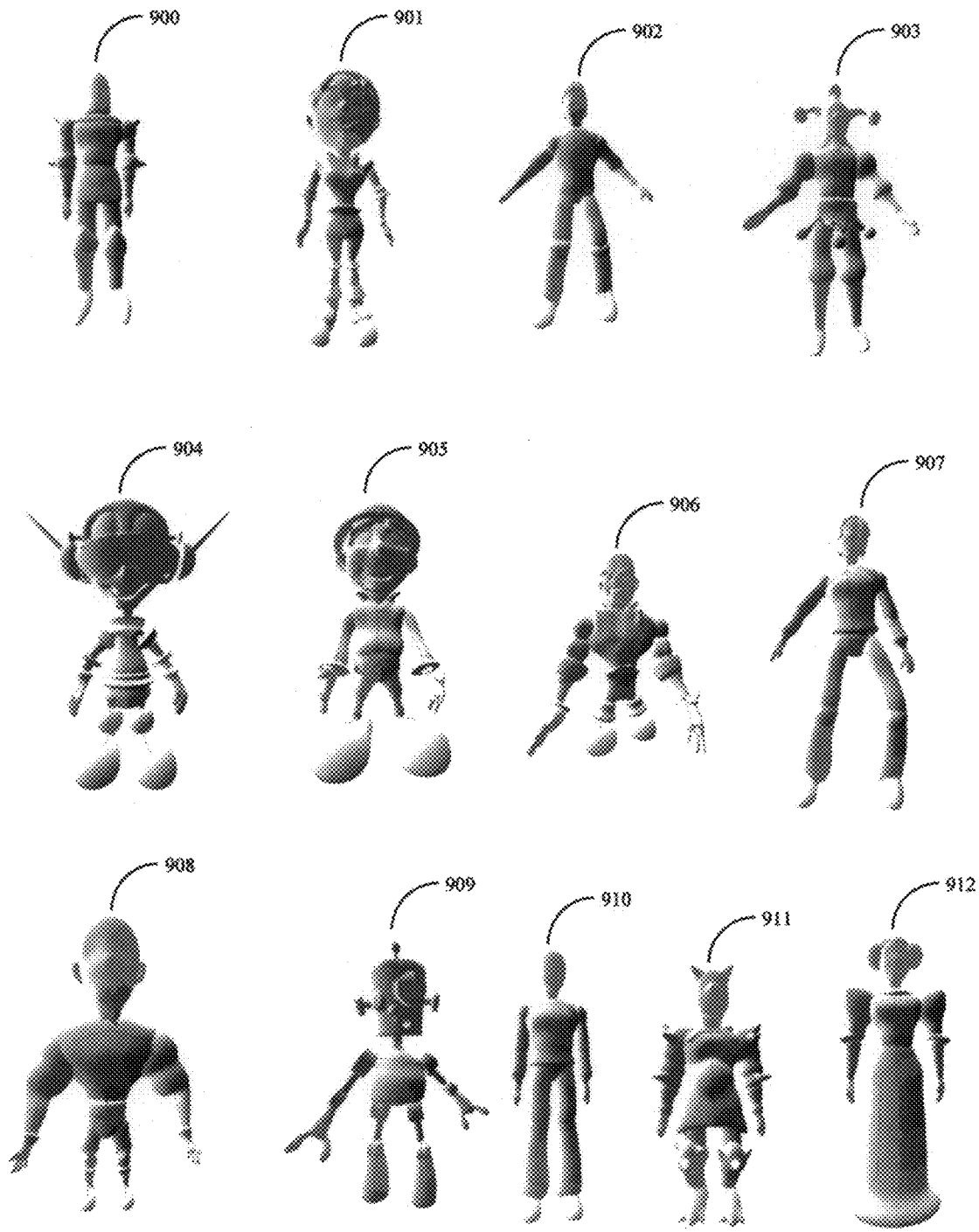
FIG. 19 depicts the segmentation of thirteen separate models via the Voronoi induction method from FIG. 4.
Figure 20:
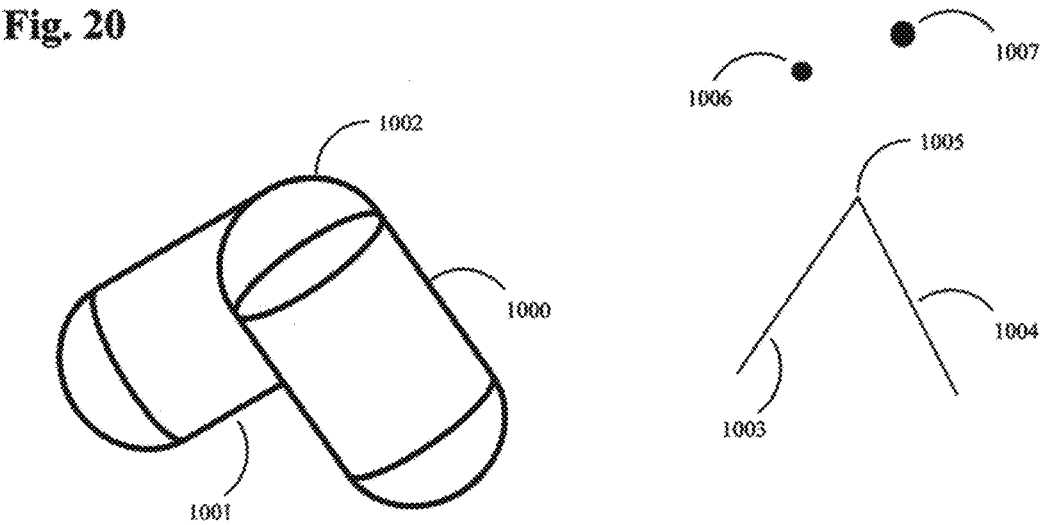
FIG. 20 depicts two pairs of overlapping sphero-cylinders, and two data values that are to be partitioned according to one of the pairs. The first pair has an associated non-zero radius for each sphero-cylinder. The second pair has a zero-valued radius for each sphero-cylinder.

The interior of a Voronoi cell $C_{i,interior}$ can be defined as $Ax=0$, where A is the augmented matrix for the system of equations that define $C_{i,interior}$. For example, we can define the interior of the Voronoi cell for 300 can be defined as:

$f_{cell,i}(s) = s,$ where:

$f_{cell,i}(S) < (s - \text{proj}_{L_{300}} s) \cdot (s - \text{proj}_{L_{300}} s) - (s - \text{proj}_{L_{306}} s) \cdot (s - \text{proj}_{L_{300}} s)$ $f_{cell,i}(s) < (s - \text{proj}_{L_{300}} s) \cdot (s - \text{proj}_{L_{300}} s) - (s - p_{802}) \cdot (s - p_{802}),$ $f_{cell,i}(s) < (\overline{L_{301}} \times \overline{L_{300}}) \times ((\overline{L_{301}} \times \overline{L_{300}}) - p_{800}) \cdot (\text{proj}_H s - p_{800}),$ $f_{cell,i}(s) > (s - p_{801}) \cdot (s - p_{801}) - (s - p_{803}) \cdot (s - p_{803}),$ $f_{cell,i}(s) > (s - \text{proj}_{L_{300}} s) \cdot (s - \text{prol}_{L_{300}} s) - (s - \text{prob}_{L_{304}} s) \cdot (s - \text{proj}_{L_{304}} s).$ FIG. 19 shows, as example of use, the results of using the method in FIG. 4 to induce a Voronoi-base segmentation of a set {900, 901, 902, 903, 904, 905, 906, 907, 908, 909, 910, 911, 912} of thirteen models. After using the method presented in FIG. 4 to segment the thirteen models in FIG. 19, all thirteen models were independently rig to the input skeleton S that was utilized as the set of generators for 11. As discussed previously in this disclosure, the automatic rigging process utilized for the models in FIG. 19 centered the joints for the input animation skeleton, used as the set of generators, in the Voronoi faces for neighboring Voronoi cells.

Figure 21:
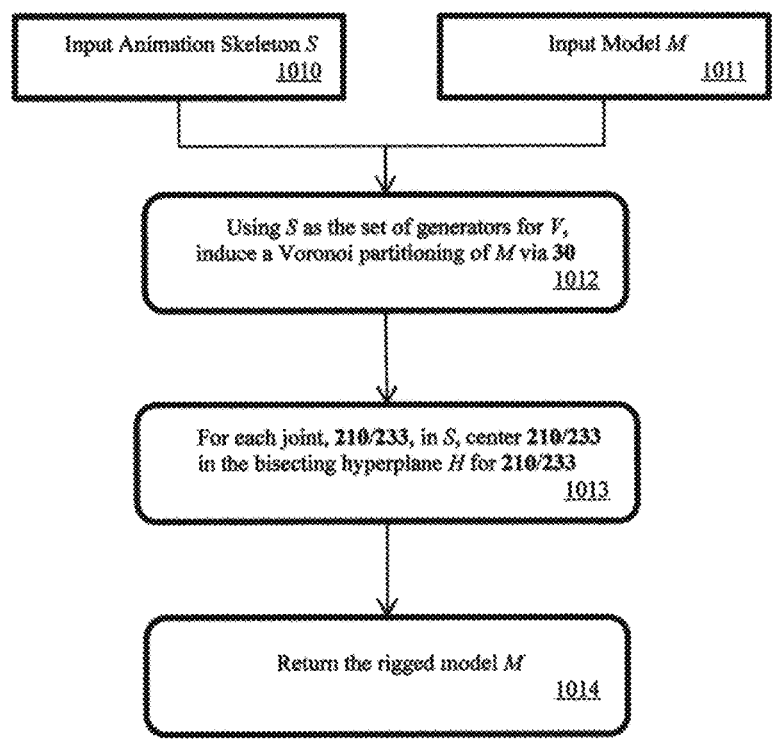
FIG. 21 depicts a method for automatically rigging an animation skeleton to a model.

FIG. 21 is a non-limiting example of an embodiment for a method for automatically rigging an animation skeleton to a model. It should be sufficiently clear to anyone familiar with the art that there are many modifications to the embodiment shown in FIG. 21 that are still covered by the intent of the depiction shown in FIG. 21. For example, an alternative embodiment would be to simultaneously import multiple animation skeletons $S_a$, from multiple sources, and autonomously rig them, in concurrent fashion, to multiple models. Another, potential embodiment would be to import a scene containing multiple models, and an animation library containing multiple animation skeletons, and then to use the method depicted in FIG. 21 to autonomously rig each model in the scene based upon the most appropriate animation skeleton from the library. Yet another possible embodiment would be to use the method depicted in FIG. 21 to autonomously rig an animation skeleton from an animation library to streaming data; potentially for the purpose of tracking and/or monitoring the behavior off an object in an observed real-world-scene.

For the particular embodiment depicted in FIG. 21, 1010 designates the application of an input animation skeleton; where said animation skeleton is to be understood as a potential set of generators for the subsequent Voronoi induction on the input model passed in 1011. 1012 uses the animation skeleton from 1010 to induce a Voronoi partition of the model from 1011 via 30. For the sake of relating the method in FIG. 21 to the current state-of-the-art in the field of computer animation, but without limiting the scope or applicability of 1012 or intent behind the embodiment shown in FIG. 21, 1012 can be viewed as skinning M from 1011 according to S from 1010. In 1013, the animation skeleton S from 1010 is then embedded in the newly partitioned model M. This embedding is done by centering the joints, which are equivalent to that depicted in 221 and 222, in S in the faces associated with each joint for the pair of Voronoi cells associated with the bones that intersect at said joints. These faces can be regarded as the bounded regions of space defined over the hyperplane $H_a$, 213 and 236, that bisect the intersecting endpoints, or joints a. This centering can be performed utilizing any number of methods. For example, the most natural method would be the average of all points $p \in M$ that lie in $H_a$ for a joint $p_a$. However, another embodiment might use the harmonic mean of all such points. Yet another embodiment could use the geometric mean. As such, the description of the joint-centering method presented here is not meant to be limiting in any way. The presented embodiment is only meant to serve as an example of one such possible embodiment for the proposed method. Lastly, the rigged model is returned in 1014.

I claim:

1. A method for partitioning values from one set into two or more new sets according to two or more intersecting line segments in three-dimensions, said method comprising:
   providing a plurality of values defining one set:
   representing said values from said one set as a collection of data or datum, each said datum corresponding to a single value of said values, each said data or datum being machine-readable:
   a second value being a mathematical entity selected from said group of geometric figures consisting of lines, points, curves, and tessellations; where said geometric figures can exist in low or high dimensional space;
   a set of intersecting line segments defined as a non-empty set of line segments that contains two or more line segments (li) such that all said line segments (li) in said set of intersecting line segments intersect at a common point (p);
      each of said line segments (li) in said set of intersecting line segments is a geometric line defined over two or more points in three-dimensional space;
      representing a pair of said intersecting line segments as a pair of finite length lines, each of said line segments having a first end and a second end, each of said line segments bounded on either said first end or said second end by a common point, such that said common point for said pair of said intersecting line segments is also known;
   deriving a plane that said pair of said intersecting line segments lie within;
   defining an angle on said plane by said pair of said intersecting line segments and between said intersecting line segments in three-dimension, and then bisecting said plane by a hyperplane, thereby defining a bisecting hyperplane, that is perpendicular to said plane defined by said pair of said intersecting line segments;

defining a bisector for said angle in said plane as a subset of said bisecting hyperplane:

whereby said bisector for said angle in said plane is a subset of said bisecting hyperplane;

where said bisecting hyperplane is a surface of separation between said data or datum that is to be associated with a first of said pair of said intersecting line segments and a second of said pair of said intersecting line segments;

defining an additional set of two hyperplanes perpendicular to said plane defined over said pair of said intersecting line segments such that a first of two said additional hyperplanes defines a chosen line segment hyperplane and contains as a subset said first of said intersecting line segments and a second of said additional hyperplanes contains as a subset said second of said intersecting line segments:

defining a perpendicular line that is perpendicular to said plane;

for every said value to be partitioned according to said pair of said intersecting line segments, said angle between said value and one of said two intersecting line segments, deterministically or arbitrarily chosen, thereby defining a chosen line segment, is computed by either:

projecting said to be partitioned value onto said plane defined by said pair of intersecting line segments and then computing an angle 1 between said chosen line and a line drawn through said value and said point of intersection of said two intersecting line segments, or, projecting said to be partitioned value onto said perpendicular line that is perpendicular to said plane, and then computing an angle 2 between said chosen line segment and a projection line that passes through said to be partitioned value and said value's projection;

using said additional chosen line segment hyperplanes by projecting said to be partitioned value onto said line that is perpendicular to said plane;

defining a new hype-plane that contains as a subset said line that passes through said to be partitioned value, said projection, and said perpendicular line:

computing an angle 3 between said chosen line segment and said line that passes through said to be partitioned value by computing the angle between said new hyperplane and said chosen line segment hyperplane;

if said angle 3 between said new hyper lane and said chosen line segment hyperplane is less than an angle between said chosen line segment and said bisecting hyperplane that contains said bisector for said angle between said two intersecting line segments then said to be partitioned value is assigned to said chosen line segment from said pair of two intersecting line segments;

if said angle 3 between said new hyperplane and said chosen line segment hyperplane is greater than said angle 4 between said chosen line segment and said bisecting hyperplane that contains said bisector for said angle between said two intersecting line segments then said to be partitioned value is assigned to said line segment from said pair of two intersecting line segments that not chosen;

wherein said assignment of said data or datum from said initial or values to said line segment (lj), or a different said line segment (lj), and according to all possible said pairs (li, lj) of intersecting line segments, from said set of 394 intersecting line segments partitions said initial set of values into said two or more new sets of values according to said set of intersecting line segments; where a maximum number of new sets or values is determined by, and proportional to, said number of line segments in said set of intersecting line segments; displaying said partitioned values to said user, or displaying said hyperplanes.

2. The method of claim 1, further comprising:

representing a Voronoi diagram as a collection of Voronoi cells defined over a set of Voronoi generators, each said Voronoi cell defined over a concave region of space delineated by a set of Voronoi vertices, Voronoi edges, and Voronoi faces, where a Voronoi vertex of said Voronoi Vertices is connected to other Voronoi vertices via a subset of said Voronoi edges, where a Voronoi edge of said Voronoi edges may be straight or curved, and each said Voronoi face is bound on at least one side by an associated said Voronoi edge and where each said Voronoi face may be planar or curved, each said Voronoi generator comprising of one or more points; for said generators containing multiple points, each said point in said generator connected to other said points in said generator by a set of generator line segments, each said generator line segment having a finite length greater than or equal to zero, but not infinie in both directions; for said generators containing line segments, a set of generator faces where each said face in said set of generator faces being bounded at least on one side by a point or a line segment;

the partitioning of said space is performed by defining each said generator in terms or said line segments and said faces that compose said generator; said line segments that compose said generators now becoming said generators for the to be derived Voronoi diagram; said space containing said Voronoi diagram being partitioned according to the proximity of a point in said space to a giving Voronoi diagram generator.

3. The method of claim 2, further comprising:

during the deriving of said Voronoi diagram;

deriving a plurality of said surface of separation as either planar or curved geometric entities;

computing respective intersections of respective two or more of said surfaces of separation, said intersections of said respective surfaces of separation being defined as either lines, curves, or point-like geometric entities that exist three-dimensional or higher dimensional space.

4. The method of claim 2, further comprising:

utilizing a Voronoi induction over an input set of precepts with respect to the data or datum as the input set of generators for said Voronoi induction;

providing an input set of data, where said input set of data is machine readable;

determining a data segmentation/cluster as a grouping of like data values from said input set of data;

defining said Voronoi diagram.

5. The method of claim 4, further comprising:
a machine readable model that is comprised of a set of said points, a set of said line segments, and a set of said faces, where;
- line segment of said set of said line segments is bound on each end by an end point where said bound end point may or may not connect all of said points in said model some other point in said model
- each said face of said set f faces is defined over at least two said line segments in said model;
- said model may have zero or more said points of said set of said points;
- said model may have zero or more said line segments of said set of said line segments;
- said model may have zero or more said faces of said set of said faces;

a set of generators for said Voronoi induction a skeleton, or animation skeleton, where;
- said skeleton d fin d over a set of skeletal points a set of skeletal line segments, also referred to as bones, bound on each end by said skeletal points where said skeletal points may or may not connect all of said skeletal points in said skeleton with some other said skeletal point in said skeleton;
- said skeleton may have zero or more said skeletal points; said skeleton may have zero or more said skeletal line segments.

6. The method of claim 5, further comprising:
providing a Voronoi diagram V induction over an input model via the use of a to-be-rigged model and an animation skeleton as a set S of generators for said V induction;
defining a plurality of bisecting polytope that are respectfully each defined as a set of said points within a specified distance of said bisecting hyperplane;
performing a subsequent embedding of animation of said skeleton to said segmented model by centering joints of said animation skeleton in said bisecting polytopes for each said joint in said animation skeleton and said associated bisecting hyperplane;
assigning bone weights to each said vertex in said model, where;
- said bone weights are to be interpreted as a value that indicates how strongly said associated vertex is correlated to an associated bone in said animation skeleton.

7. The method of claim 2, further comprising:
representing said Voronoi diagram as a collection of said Voronoi cells defined over a set of said Voronoi generators,
- each said Voronoi cell defined over a concave region of space delineated by a set of said Voronoi vertices, said Voronoi edges, and said Voronoi faces, where said Voronoi vertices are connected to other said Voronoi vertices via said Voronoi edges, where said Voronoi edges may be straight or curved, and each said Voronoi face is bound on at least one side by an associated said Voronoi edge and where each said Voronoi face may be planar or curved,
- each said Voronoi generator comprising of one or more said points, each said point in said generator connected to other said points in said generator by one or more said line segments, each said line segment having a finite length greater than or equal to zero, but not infinite in both directions, each said face in said generator being bounded at least on one said side by a point of said points or a line segment of said line segments;

said generators for the to be derived Voronoi diagrams are defined as a set of players of a game G where;
- said game G is a mathematical game defined over a triple $<N, A, u>$ where:
  - said N is said set of n players, which said N is the set of players for the current game and is the same as said set of generators for said to be constructed Voronoi diagram,
  - said $A=A_1 \times \ldots \times A_n$, where $A=A_i$ and is the finite of actions for player i of said n players, or the $i^{th}$ generator for said to be construction Voronoi diagram, such that:
    - an action for said game G with respect to said player i is a decision to assign the to be partitioned value to said current player i or to an alternative player j in said N of players for said game G;
  - and said $u=(u_i, \ldots, u_n)$, where $u_i:A \to \mathscr{R}$ is a utility function for said game G such that:
    - said utility function $u_i$ for said glamor i taking an action $a_{i,k}$ to assign a data value from said input data to one such said player is a function of the distance of said data value to said player;
    - said derived Voronoi diagram is a solution to said game G.

* * * * *